US011913166B2

(12) United States Patent
Purcell et al.

(10) Patent No.: US 11,913,166 B2
(45) Date of Patent: Feb. 27, 2024

(54) FIBER REINFORCED TISSUE COMPOSITES

(71) Applicant: MODERN MEADOW, INC., Nutley, NJ (US)

(72) Inventors: Brendan Patrick Purcell, Nutley, NJ (US); Gabor Forgacs, Nutley, NJ (US)

(73) Assignee: MODERN MEADOW, INC., Nutley, NJ (US)

( * ) Notice: Subject to any disclaimer, the term of this patent is extended or adjusted under 35 U.S.C. 154(b) by 470 days.

(21) Appl. No.: 15/761,209

(22) PCT Filed: Sep. 21, 2016

(86) PCT No.: PCT/US2016/052891
§ 371 (c)(1),
(2) Date: Mar. 19, 2018

(87) PCT Pub. No.: WO2017/053433
PCT Pub. Date: Mar. 30, 2017

(65) Prior Publication Data
US 2018/0230644 A1  Aug. 16, 2018

Related U.S. Application Data

(60) Provisional application No. 62/221,521, filed on Sep. 21, 2015.

(51) Int. Cl.
*D06N 3/00* (2006.01)
*C12N 5/00* (2006.01)
*C14C 3/06* (2006.01)

(52) U.S. Cl.
CPC ......... *D06N 3/0006* (2013.01); *C12N 5/0068* (2013.01); *C14C 3/06* (2013.01);
(Continued)

(58) Field of Classification Search
CPC ...... D06N 3/0006; D06N 3/00; D06N 3/0011; C12N 5/0068; C14C 3/06
(Continued)

(56) References Cited

U.S. PATENT DOCUMENTS 2,059,856 A   11/1936 Eastman et al.
2,673,171 A   3/1954 Leon et al.
(Continued)

FOREIGN PATENT DOCUMENTS

CA    2306346 A1   1/1999
CN    1163642 A    10/1997
(Continued)

OTHER PUBLICATIONS

JP-05184661-A machine translation (Year: 1993).*
(Continued)

*Primary Examiner* — Vincent Tatesure
(74) *Attorney, Agent, or Firm* — Sterne, Kessler, Goldstein & Fox P.L.L.C.

(57) ABSTRACT

Engineered, reinforced leather materials (engineered leathers) including a composite of a fibrous matrix that has been tanned to allow crosslinking of the fibrous matrix to the collagen formed by cultured cells (e.g., fibroblasts). These engineered leathers may be referred to as fiber-reinforced biological tissue composites. Also described herein are methods of making such fiber-reinforced biological tissue composites.

12 Claims, 4 Drawing Sheets

(52) U.S. Cl.
CPC .............. D06N 3/00 (2013.01); D06N 3/0011 (2013.01); *C12N 2533/50* (2013.01)

(58) Field of Classification Search
USPC ........................................................ 442/153
See application file for complete search history.

(56) References Cited

U.S. PATENT DOCUMENTS

| | | |
|---|---|---|
| 2,934,446 A | 4/1960 | Highberger et al. |
| 3,073,714 A | 1/1963 | Shu-Tung et al. |
| 3,122,599 A | 2/1964 | Shu-Tung et al. |
| 3,136,682 A | 6/1964 | Shu-Tung et al. |
| 3,483,016 A | 12/1969 | McCool et al. |
| 3,497,363 A | 2/1970 | Fox, Jr. et al. |
| 3,512,993 A | 5/1970 | Conley et al. |
| 3,537,871 A | 11/1970 | Kaneko et al. |
| 3,562,820 A | 2/1971 | Braun et al. |
| 3,656,881 A | 4/1972 | Hemwall |
| 3,684,732 A | 8/1972 | Grabauskas et al. |
| 3,728,207 A | 4/1973 | Heling et al. |
| 3,811,832 A | 5/1974 | Briggs |
| 3,873,478 A | 3/1975 | Comte et al. |
| 3,921,313 A | 11/1975 | Mahide et al. |
| 3,956,560 A | 5/1976 | Smith et al. |
| 3,979,532 A | 9/1976 | Muck et al. |
| 4,089,333 A | 5/1978 | Utsuo et al. |
| 4,215,051 A | 7/1980 | Palmer et al. |
| 4,247,279 A | 1/1981 | Masters |
| 4,291,992 A | 9/1981 | Barr et al. |
| 4,294,241 A | 10/1981 | Miyata |
| 4,404,033 A | 9/1983 | Steffan |
| 4,407,956 A | 10/1983 | Howell |
| 4,455,206 A | 6/1984 | Funabashi et al. |
| 4,464,428 A | 8/1984 | Ebert et al. |
| 4,465,472 A | 8/1984 | Urbaniak |
| 4,525,169 A | 6/1985 | Higuchi et al. |
| 4,526,581 A | 7/1985 | Prentiss et al. |
| 4,532,929 A | 8/1985 | Mattei et al. |
| 4,536,475 A | 8/1985 | Anderson |
| 4,564,597 A | 1/1986 | Lerner et al. |
| 4,585,139 A | 4/1986 | Bronson et al. |
| 4,640,529 A | 2/1987 | Katz |
| 4,646,106 A | 2/1987 | Howkins |
| 4,665,492 A | 5/1987 | Masters |
| 4,673,304 A | 6/1987 | Liu et al. |
| 4,684,611 A | 8/1987 | Schilperoort et al. |
| 4,736,866 A | 4/1988 | Leder et al. |
| 4,772,141 A | 9/1988 | Sanders et al. |
| 4,842,575 A | 6/1989 | Hoffman et al. |
| 4,889,438 A | 12/1989 | Forsyth et al. |
| 4,896,980 A | 1/1990 | Sanders et al. |
| 4,921,365 A | 5/1990 | Sanders et al. |
| 4,931,546 A | 6/1990 | Tardy et al. |
| 4,945,050 A | 7/1990 | Sanford et al. |
| 4,948,280 A | 8/1990 | Sanders et al. |
| 4,969,758 A | 11/1990 | Sanders et al. |
| 4,970,168 A | 11/1990 | Tumer |
| 4,980,112 A | 12/1990 | Masters |
| 4,980,403 A | 12/1990 | Bateman et al. |
| 5,016,121 A | 5/1991 | Peddle et al. |
| 5,039,297 A | 8/1991 | Masters |
| 5,040,911 A | 8/1991 | Sanders et al. |
| 5,108,424 A | 4/1992 | Hoffman et al. |
| 5,134,178 A | 7/1992 | Nishibori |
| 5,134,569 A | 7/1992 | Masters |
| 5,153,067 A | 10/1992 | Yoshida et al. |
| 5,171,273 A | 12/1992 | Silver et al. |
| 5,185,253 A | 2/1993 | Tumer |
| 5,201,745 A | 4/1993 | Tayot et al. |
| 5,204,055 A | 4/1993 | Sachs et al. |
| 5,216,606 A | 6/1993 | Lentz et al. |
| 5,229,112 A | 7/1993 | Obukowicz et al. |
| 5,304,730 A | 4/1994 | Lawson et al. |
| 5,349,124 A | 9/1994 | Fischhoff et al. |
| 5,362,865 A | 11/1994 | Austin |
| 5,378,619 A | 1/1995 | Rogers |
| 5,424,412 A | 6/1995 | Brown et al. |
| 5,487,992 A | 1/1996 | Capecchi et al. |
| 5,490,962 A | 2/1996 | Cima et al. |
| 5,492,937 A | 2/1996 | Bogentoft et al. |
| 5,495,071 A | 2/1996 | Fischhoff et al. |
| 5,503,999 A | 4/1996 | Jilka et al. |
| 5,510,253 A | 4/1996 | Mitsky et al. |
| 5,534,327 A | 7/1996 | Nishi et al. |
| 5,546,313 A | 8/1996 | Masters |
| 5,589,612 A | 12/1996 | Jilka et al. |
| 5,593,859 A | 1/1997 | Prockop et al. |
| 5,593,874 A | 1/1997 | Brown et al. |
| 5,599,695 A | 2/1997 | Pease et al. |
| 5,602,321 A | 2/1997 | John |
| 5,605,662 A | 2/1997 | Heller et al. |
| 5,614,396 A | 3/1997 | Bradley et al. |
| 5,627,061 A | 5/1997 | Barry et al. |
| 5,631,152 A | 5/1997 | Fry et al. |
| 5,633,435 A | 5/1997 | Barry et al. |
| 5,658,603 A | 8/1997 | Andersen et al. |
| 5,658,802 A | 8/1997 | Hayes et al. |
| 5,659,122 A | 8/1997 | Austin |
| 5,662,731 A | 9/1997 | Andersen et al. |
| 5,689,052 A | 11/1997 | Brown et al. |
| 5,697,324 A | 12/1997 | Van Der Lely |
| 5,702,717 A | 12/1997 | Cha et al. |
| 5,714,560 A | 2/1998 | Denzinger et al. |
| 5,716,837 A | 2/1998 | Barry et al. |
| 5,739,832 A | 4/1998 | Heinzl et al. |
| 5,763,241 A | 6/1998 | Fischhoff et al. |
| 5,763,245 A | 6/1998 | Greenplate et al. |
| 5,792,933 A | 8/1998 | Ma |
| 5,797,898 A | 8/1998 | Santini, Jr. et al. |
| 5,798,779 A | 8/1998 | Nakayasu et al. |
| 5,804,425 A | 9/1998 | Barry et al. |
| 5,824,838 A | 10/1998 | Melmed et al. |
| 5,831,070 A | 11/1998 | Pease et al. |
| 5,859,347 A | 1/1999 | Brown et al. |
| 5,866,121 A | 2/1999 | Coffino et al. |
| 5,869,720 A | 2/1999 | John |
| 5,929,208 A | 7/1999 | Heller et al. |
| 5,932,056 A | 8/1999 | Mark et al. |
| 5,932,439 A | 8/1999 | Bogosian |
| 5,945,319 A | 8/1999 | Keogh |
| 5,959,091 A | 9/1999 | Watrud et al. |
| 5,959,179 A | 9/1999 | Hinchee et al. |
| 5,981,841 A | 11/1999 | Santino et al. |
| 6,087,102 A | 7/2000 | Chenchik et al. |
| 6,103,528 A | 8/2000 | An et al. |
| 6,109,717 A | 8/2000 | Kane et al. |
| 6,123,861 A | 9/2000 | Santini, Jr. et al. |
| 6,132,468 A | 10/2000 | Mansmann |
| 6,139,831 A | 10/2000 | Shivashankar et al. |
| 6,171,797 B1 | 1/2001 | Perbost |
| 6,197,575 B1 | 3/2001 | Griffith et al. |
| 6,239,273 B1 | 5/2001 | Pease et al. |
| 6,261,493 B1 | 7/2001 | Gaylo et al. |
| 6,277,600 B1 | 8/2001 | Tomita et al. |
| 6,336,480 B2 | 1/2002 | Gaylo et al. |
| 6,365,650 B1 | 4/2002 | Chen et al. |
| 6,368,361 B1 | 4/2002 | Yayabe et al. |
| 6,383,549 B1 | 5/2002 | Agostinelli |
| 6,387,707 B1 | 5/2002 | Seul et al. |
| 6,394,585 B1 | 5/2002 | Ross |
| 6,402,403 B1 | 6/2002 | Speakman |
| 6,419,883 B1 | 7/2002 | Blanchard |
| 6,428,978 B1 | 8/2002 | Olsen et al. |
| 6,451,346 B1 | 9/2002 | Shah et al. |
| 6,454,811 B1 | 9/2002 | Sherwood et al. |
| 6,455,311 B1 | 9/2002 | Vacanti |
| 6,495,102 B1 | 12/2002 | Suslick et al. |
| 6,497,510 B1 | 12/2002 | Delametter et al. |
| 6,511,958 B1 | 1/2003 | Atkinson et al. |
| 6,514,518 B2 | 2/2003 | Monkhouse et al. |
| 6,517,648 B1 | 2/2003 | Bouchette et al. |
| 6,527,378 B2 | 3/2003 | Rausch et al. |
| 6,536,873 B1 | 3/2003 | Lee et al. |
| 6,536,895 B2 | 3/2003 | Kashiwagi et al. |

(56) References Cited

U.S. PATENT DOCUMENTS

| | | |
|---|---|---|
| 6,538,089 B1 | 3/2003 | Samra et al. |
| 6,543,872 B2 | 4/2003 | Ohtsuka et al. |
| 6,547,994 B1 | 4/2003 | Monkhouse et al. |
| 6,548,263 B1 | 4/2003 | Kapur et al. |
| 6,550,904 B2 | 4/2003 | Koitabashi et al. |
| 6,561,626 B1 | 5/2003 | Min et al. |
| 6,561,642 B2 | 5/2003 | Gonzalez |
| 6,565,176 B2 | 5/2003 | Anderson et al. |
| 6,596,304 B1 | 7/2003 | Bayon et al. |
| 6,708,531 B1 | 3/2004 | Thanikaivelan et al. |
| 6,733,859 B2 | 5/2004 | Yoneda et al. |
| 6,762,336 B1 | 7/2004 | MacPhee et al. |
| 6,800,384 B2 | 10/2004 | Suzuki et al. |
| 6,835,390 B1 | 12/2004 | Vein |
| 6,942,830 B2 | 9/2005 | Muelhaupt et al. |
| 6,979,670 B1 | 12/2005 | Lyngstadaas et al. |
| 7,004,978 B2 | 2/2006 | Kando et al. |
| 7,051,654 B2 | 5/2006 | Boland et al. |
| 7,056,845 B2 | 6/2006 | Waeber et al. |
| 7,166,464 B2 | 1/2007 | McAllister et al. |
| 7,270,829 B2 | 9/2007 | Van Eelen |
| 7,625,198 B2 | 12/2009 | Lipson et al. |
| 7,645,818 B2 | 1/2010 | Jong |
| 7,812,075 B2 | 10/2010 | Hong |
| 7,882,717 B2 | 2/2011 | Widdemer |
| 8,076,137 B2 | 12/2011 | McAllister et al. |
| 8,076,385 B2 | 12/2011 | Ohama |
| 8,153,176 B2 | 4/2012 | Etayo Garralda et al. |
| 8,188,230 B2 | 5/2012 | Van Heerde et al. |
| 8,328,878 B2 | 12/2012 | Zhang |
| 8,329,601 B2 | 12/2012 | Shi et al. |
| 8,343,522 B2 | 1/2013 | Pohl et al. |
| 8,378,010 B2 | 2/2013 | Browning et al. |
| 8,491,668 B2 | 7/2013 | Hinestroza et al. |
| 8,519,031 B2 | 8/2013 | Parker et al. |
| 8,628,837 B2 | 1/2014 | Kusuura |
| 8,679,197 B2 | 3/2014 | Hinestroza et al. |
| 8,680,224 B2 | 3/2014 | Zhang et al. |
| 8,703,216 B2 | 4/2014 | Forgacs et al. |
| 8,741,415 B2 | 6/2014 | Kusuura |
| 8,785,195 B2 | 7/2014 | Takeuchi et al. |
| 8,916,263 B2 | 12/2014 | Kusuura |
| 8,916,668 B2 | 12/2014 | Parker et al. |
| 9,023,619 B2 | 5/2015 | De Boer |
| 9,103,066 B2 | 8/2015 | Kusuura |
| 9,156,950 B2 | 10/2015 | Garralda et al. |
| 9,163,205 B2 | 10/2015 | Sivik et al. |
| 9,163,338 B2 | 10/2015 | Schauer et al. |
| 9,181,404 B2 | 11/2015 | Neresini et al. |
| 9,259,455 B2 | 2/2016 | Song et al. |
| 9,332,779 B2 | 5/2016 | Marga |
| 9,416,303 B2 | 8/2016 | Parker et al. |
| 9,428,817 B2 | 8/2016 | Greene |
| 9,439,813 B2 | 9/2016 | Terada |
| 9,518,106 B2 | 12/2016 | Saeidi et al. |
| 9,539,363 B2 | 1/2017 | Shimp |
| 9,683,070 B2 | 6/2017 | Zhang et al. |
| 9,708,757 B2 | 7/2017 | Viladot Petit et al. |
| 9,733,393 B2 | 8/2017 | Liu et al. |
| 9,752,122 B2 | 9/2017 | Marga et al. |
| 9,816,019 B2 | 11/2017 | Parker et al. |
| 9,821,089 B2 | 11/2017 | Haj-Ali et al. |
| 9,909,044 B2 | 3/2018 | Parker et al. |
| 9,913,925 B2 | 3/2018 | Chmielewski |
| 9,988,318 B2 | 6/2018 | Schrader et al. |
| 10,124,543 B1 | 11/2018 | Tymon et al. |
| 10,131,096 B1 | 11/2018 | Tymon et al. |
| 10,138,595 B1 | 11/2018 | Tymon |
| 10,259,191 B2 | 4/2019 | Wijesena et al. |
| 10,273,549 B2 | 4/2019 | Helgason et al. |
| 10,294,611 B2 | 5/2019 | Eryilmaz et al. |
| 10,301,440 B2 | 5/2019 | Purcell et al. |
| 10,370,504 B2 | 8/2019 | Purcell et al. |
| 10,370,505 B2 | 8/2019 | Purcell et al. |
| 10,465,103 B2 | 11/2019 | Parker et al. |
| 10,519,285 B2 | 12/2019 | Purcell et al. |
| 10,526,516 B2 | 1/2020 | Parker et al. |
| 10,745,601 B2 | 8/2020 | Parker et al. |
| 10,913,880 B2 | 2/2021 | Parker et al. |
| 11,001,679 B2 | 5/2021 | Purcell et al. |
| 11,286,354 B2 | 3/2022 | Purcell et al. |
| 2002/0031500 A1 | 3/2002 | MacLaughlin et al. |
| 2002/0059049 A1 | 5/2002 | Bradbury et al. |
| 2002/0064808 A1 | 5/2002 | Mutz et al. |
| 2002/0064809 A1 | 5/2002 | Mutz et al. |
| 2002/0084290 A1 | 7/2002 | Materna |
| 2002/0089561 A1 | 7/2002 | Weitzel et al. |
| 2002/0090720 A1 | 7/2002 | Mutz et al. |
| 2002/0106412 A1 | 8/2002 | Rowe et al. |
| 2002/0142391 A1 | 10/2002 | Kivirikko et al. |
| 2002/0160109 A1 | 10/2002 | Yeo et al. |
| 2002/0164319 A1 | 11/2002 | Khaw et al. |
| 2002/0173586 A1 | 11/2002 | Jeong et al. |
| 2002/0182633 A1 | 12/2002 | Chen et al. |
| 2002/0188349 A1 | 12/2002 | McAllister et al. |
| 2003/0012805 A1 | 1/2003 | Chen et al. |
| 2003/0027332 A1 | 2/2003 | Lafrance et al. |
| 2003/0031500 A1 | 2/2003 | Bouveresse |
| 2003/0032203 A1 | 2/2003 | Sabatini et al. |
| 2003/0059537 A1 | 3/2003 | Chilkoti et al. |
| 2003/0100824 A1 | 5/2003 | Warren et al. |
| 2003/0113433 A1 | 6/2003 | Tempesta |
| 2003/0118560 A1 | 6/2003 | Kelly et al. |
| 2003/0129699 A1 | 7/2003 | Perret et al. |
| 2003/0134120 A1 | 7/2003 | Kim et al. |
| 2003/0153078 A1 | 8/2003 | Libera et al. |
| 2003/0175410 A1 | 9/2003 | Campbell et al. |
| 2003/0190438 A1 | 10/2003 | Suzuki et al. |
| 2003/0207638 A1 | 11/2003 | Bowlin et al. |
| 2004/0005663 A1 | 1/2004 | Bell et al. |
| 2004/0018226 A1 | 1/2004 | Wnek et al. |
| 2004/0018592 A1 | 1/2004 | Bell et al. |
| 2004/0037813 A1 | 2/2004 | Simpson et al. |
| 2004/0039727 A1 | 2/2004 | Dessloch et al. |
| 2004/0046277 A1 | 3/2004 | Buerger et al. |
| 2004/0116032 A1 | 6/2004 | Bowlin et al. |
| 2004/0219133 A1 | 11/2004 | Lyles |
| 2004/0237208 A1 | 12/2004 | Day |
| 2005/0084719 A1 | 4/2005 | Yoshimoto et al. |
| 2005/0118326 A1 | 6/2005 | Anfinsen et al. |
| 2005/0129730 A1 | 6/2005 | Pang et al. |
| 2005/0148727 A1 | 7/2005 | Ajbani et al. |
| 2005/0163912 A1 | 7/2005 | White |
| 2005/0202268 A1 | 9/2005 | Kotter et al. |
| 2005/0261427 A1 | 11/2005 | Saito |
| 2005/0276791 A1 | 12/2005 | Hansford et al. |
| 2006/0121006 A1 | 6/2006 | Chancellor et al. |
| 2006/0141479 A1 | 6/2006 | Song et al. |
| 2006/0264135 A1 | 11/2006 | Netravali et al. |
| 2006/0270037 A1 | 11/2006 | Kato et al. |
| 2007/0088341 A1 | 4/2007 | Skiba et al. |
| 2007/0142916 A1 | 6/2007 | Olson et al. |
| 2007/0184742 A1 | 8/2007 | Coulson et al. |
| 2007/0231787 A1 | 10/2007 | Voelker |
| 2007/0238167 A1 | 10/2007 | Perez et al. |
| 2007/0292702 A1 | 12/2007 | Saumweber |
| 2008/0070304 A1 | 3/2008 | Forgacs et al. |
| 2008/0103287 A1 | 5/2008 | Chino et al. |
| 2008/0171994 A1 | 7/2008 | Williams et al. |
| 2008/0242822 A1 | 10/2008 | West |
| 2009/0005867 A1 | 1/2009 | Lefranc et al. |
| 2009/0041907 A1 | 2/2009 | Etayo Garralda et al. |
| 2009/0069893 A1 | 3/2009 | Paukshto et al. |
| 2009/0075382 A1* | 3/2009 | Sachlos .................. A61L 27/58 |
| | | 435/398 |
| 2009/0142307 A1 | 6/2009 | Athanasiou et al. |
| 2009/0162896 A1 | 6/2009 | Scheibel |
| 2009/0208466 A1 | 8/2009 | Yoo et al. |
| 2009/0209823 A1 | 8/2009 | Yamane |
| 2009/0248145 A1 | 10/2009 | Chan et al. |
| 2009/0295022 A1 | 12/2009 | Kumar |
| 2010/0016872 A1 | 1/2010 | Bayon et al. |
| 2010/0041134 A1 | 2/2010 | Forgacs et al. |
| 2010/0087854 A1 | 4/2010 | Stopek et al. |

(56) References Cited

U.S. PATENT DOCUMENTS

| | | |
|---|---|---|
| 2010/0189712 A1 | 7/2010 | L'Heureux et al. |
| 2010/0256314 A1 | 10/2010 | Marsden et al. |
| 2010/0325811 A1 | 12/2010 | Kashiwagura et al. |
| 2011/0076326 A1 | 3/2011 | Caillard et al. |
| 2011/0151231 A1 | 6/2011 | Chomarat et al. |
| 2011/0151563 A1 | 6/2011 | Paukshto et al. |
| 2011/0165301 A1 | 7/2011 | Blumenthal |
| 2011/0212179 A1 | 9/2011 | Liu |
| 2011/0212501 A1 | 9/2011 | Yoo |
| 2011/0250308 A1 | 10/2011 | Jun et al. |
| 2011/0288274 A1 | 11/2011 | Russell et al. |
| 2012/0010119 A1 | 1/2012 | Cunningham |
| 2012/0023777 A1 | 2/2012 | Greene |
| 2012/0040119 A1 | 2/2012 | Gagnieu et al. |
| 2012/0053689 A1 | 3/2012 | Martin et al. |
| 2012/0116053 A1 | 5/2012 | Mirochnitchenko et al. |
| 2012/0116568 A1 | 5/2012 | Murphy et al. |
| 2012/0164200 A1 | 6/2012 | Qin et al. |
| 2012/0190473 A1 | 7/2012 | Swist |
| 2012/0202722 A1 | 8/2012 | Laudenklos et al. |
| 2012/0230950 A1 | 9/2012 | Niklason et al. |
| 2012/0273993 A1 | 11/2012 | Shoseyov et al. |
| 2012/0276203 A1 | 11/2012 | Selim et al. |
| 2012/0316646 A1 | 12/2012 | Gretzer et al. |
| 2013/0029008 A1 | 1/2013 | Forgacs et al. |
| 2013/0131781 A1 | 5/2013 | Greenhalgh et al. |
| 2013/0142763 A1 | 6/2013 | Carlson et al. |
| 2013/0215598 A1 | 8/2013 | Guzan et al. |
| 2013/0255003 A1* | 10/2013 | Forgacs .................. C08H 1/06 8/94.2 |
| 2013/0256064 A1 | 10/2013 | Bongaerts et al. |
| 2013/0287896 A1 | 10/2013 | Harel et al. |
| 2013/0337711 A1 | 12/2013 | Wool |
| 2014/0005663 A1 | 1/2014 | Heard et al. |
| 2014/0017284 A1 | 1/2014 | Yang et al. |
| 2014/0021703 A1 | 1/2014 | Scharf et al. |
| 2014/0093618 A1 | 4/2014 | Forgacs et al. |
| 2014/0193477 A1 | 7/2014 | Chaikof et al. |
| 2014/0205729 A1 | 7/2014 | Didzbalis et al. |
| 2014/0215850 A1 | 8/2014 | Redl et al. |
| 2014/0264079 A1 | 9/2014 | Tarahomi et al. |
| 2015/0013299 A1 | 1/2015 | Haj-Ali et al. |
| 2015/0079238 A1 | 3/2015 | Marga et al. |
| 2015/0216216 A1 | 8/2015 | Marga |
| 2015/0306276 A1 | 10/2015 | Shimp |
| 2016/0097109 A1 | 4/2016 | Forgacs et al. |
| 2016/0097154 A1 | 4/2016 | Dumbrique et al. |
| 2016/0106674 A1 | 4/2016 | Scalesciani |
| 2016/0227831 A1 | 8/2016 | Marga |
| 2016/0250831 A1 | 9/2016 | Gladish et al. |
| 2016/0280960 A1 | 9/2016 | Leimer et al. |
| 2016/0287747 A1 | 10/2016 | Schallenberger |
| 2016/0348078 A1 | 12/2016 | Forgacs et al. |
| 2016/0376737 A1* | 12/2016 | Marga .................... C12P 21/00 442/334 |
| 2017/0152301 A1 | 6/2017 | Koob et al. |
| 2017/0233537 A1 | 8/2017 | Purcell et al. |
| 2017/0233836 A1 | 8/2017 | Jakab et al. |
| 2017/0233943 A1 | 8/2017 | Purcell et al. |
| 2017/0233944 A1 | 8/2017 | Purcell et al. |
| 2017/0233945 A1 | 8/2017 | Purcell et al. |
| 2017/0298565 A1 | 10/2017 | Eryilmaz et al. |
| 2018/0084792 A1 | 3/2018 | Garcia et al. |
| 2018/0105659 A1 | 4/2018 | Hu et al. |
| 2018/0119318 A1 | 5/2018 | Morales |
| 2018/0237592 A1 | 8/2018 | Celia |
| 2018/0371665 A1 | 12/2018 | Lin et al. |
| 2019/0024303 A1 | 1/2019 | Lee et al. |
| 2019/0032275 A1 | 1/2019 | Zhou et al. |
| 2019/0136060 A1 | 5/2019 | Helgason et al. |
| 2019/0144957 A1 | 5/2019 | Purcell et al. |
| 2019/0203000 A1 | 7/2019 | Purcell et al. |
| 2019/0226141 A1 | 7/2019 | Aydin et al. |
| 2020/0199695 A1 | 6/2020 | Forgacs et al. |
| 2020/0207932 A1 | 7/2020 | Purcell et al. |
| 2020/0231805 A1 | 7/2020 | Teglia et al. |
| 2020/0370215 A1 | 11/2020 | Marga |
| 2021/0300994 A1 | 9/2021 | Schachtschneider et al. |
| 2021/0355326 A1 | 11/2021 | Broadbent |
| 2022/0106733 A1 | 4/2022 | Cai et al. |
| 2022/0127784 A1 | 4/2022 | Handlin, Jr. et al. |
| 2022/0153993 A1 | 5/2022 | Teglia et al. |

FOREIGN PATENT DOCUMENTS

| | | |
|---|---|---|
| CN | 1420949 A | 5/2003 |
| CN | 1488016 A | 4/2004 |
| CN | 1583884 A | 2/2005 |
| CN | 1298901 C | 2/2007 |
| CN | 101946852 A | 1/2011 |
| CN | 102016077 A | 4/2011 |
| CN | 102105075 A | 6/2011 |
| CN | 102586995 A | 7/2012 |
| CN | 102781490 A | 11/2012 |
| CN | 102906318 A | 1/2013 |
| CN | 203021702 U | 6/2013 |
| CN | 203021703 U | 6/2013 |
| CN | 203021840 U | 6/2013 |
| CN | 203021842 U | 6/2013 |
| CN | 203021843 U | 6/2013 |
| CN | 103231577 A | 8/2013 |
| CN | 103233321 A | 8/2013 |
| CN | 103233322 A | 8/2013 |
| CN | 103233324 A | 8/2013 |
| CN | 103233325 A | 8/2013 |
| CN | 103233326 A | 8/2013 |
| CN | 103255504 A | 8/2013 |
| CN | 103255506 A | 8/2013 |
| CN | 103255508 A | 8/2013 |
| CN | 103255509 A | 8/2013 |
| CN | 103255579 A | 8/2013 |
| CN | 103255581 A | 8/2013 |
| CN | 103255586 A | 8/2013 |
| CN | 103256796 A | 8/2013 |
| CN | 103264552 A | 8/2013 |
| CN | 103266425 A | 8/2013 |
| CN | 103276531 A | 9/2013 |
| CN | 203174344 U | 9/2013 |
| CN | 203174410 U | 9/2013 |
| CN | 203174411 U | 9/2013 |
| CN | 203174412 U | 9/2013 |
| CN | 203174413 U | 9/2013 |
| CN | 203174414 U | 9/2013 |
| CN | 203174415 U | 9/2013 |
| CN | 203174416 U | 9/2013 |
| CN | 203174417 U | 9/2013 |
| CN | 203174418 U | 9/2013 |
| CN | 203174419 U | 9/2013 |
| CN | 203291935 U | 11/2013 |
| CN | 203295678 U | 11/2013 |
| CN | 203295679 U | 11/2013 |
| CN | 203295689 U | 11/2013 |
| CN | 203295690 U | 11/2013 |
| CN | 203295794 U | 11/2013 |
| CN | 203295796 U | 11/2013 |
| CN | 203298579 U | 11/2013 |
| CN | 203307577 U | 11/2013 |
| CN | 103436168 A | 12/2013 |
| CN | 104233778 A | 12/2014 |
| CN | 102995165 B | 1/2015 |
| CN | 103252276 B | 1/2015 |
| CN | 204112009 U | 1/2015 |
| CN | 204112011 U | 1/2015 |
| CN | 103014924 B | 2/2015 |
| CN | 103231576 B | 4/2015 |
| CN | 103255653 B | 4/2015 |
| CN | 104603293 A | 5/2015 |
| CN | 104695205 A | 6/2015 |
| CN | 105102711 A | 11/2015 |
| CN | 205347859 U | 6/2016 |
| CN | 205361168 U | 7/2016 |
| CN | 106457761 A | 2/2017 |
| EP | 0067553 A2 | 12/1982 |
| EP | 0078040 A2 | 5/1983 |

(56) References Cited

FOREIGN PATENT DOCUMENTS

| | | | |
|---|---|---|---|
| EP | 0089029 | A2 | 9/1983 |
| EP | 0388854 | A2 | 9/1990 |
| EP | 0421450 | A2 | 4/1991 |
| EP | 0426641 | A2 | 5/1991 |
| EP | 0470399 | A2 | 2/1992 |
| EP | 0531273 | A2 | 3/1993 |
| EP | 0578627 | A1 | 1/1994 |
| EP | 0388854 | B1 | 11/1994 |
| EP | 0709462 | A2 | 5/1996 |
| EP | 1319415 | A1 | 6/2003 |
| EP | 1 589 098 | | 10/2005 |
| EP | 1589091 | A1 | 10/2005 |
| EP | 1232182 | B1 | 10/2007 |
| EP | 1785252 | B1 | 9/2008 |
| EP | 2003239 | A1 | 12/2008 |
| EP | 2090584 | A1 | 8/2009 |
| EP | 2148887 | A2 | 2/2010 |
| EP | 2319337 | A1 | 5/2011 |
| EP | 2576661 | A2 | 4/2013 |
| EP | 2618998 | A1 | 7/2013 |
| EP | 2148887 | B1 | 4/2014 |
| EP | 2721941 | A1 | 4/2014 |
| EP | 3165556 | A2 | 5/2017 |
| EP | 2464612 | B1 | 7/2018 |
| EP | 2880116 | B1 | 2/2020 |
| FR | 2188610 | A5 | 1/1974 |
| GB | 723214 | A | 2/1955 |
| GB | 723215 | A | 2/1955 |
| GB | 992585 | A | 5/1965 |
| GB | 1024769 | A | 4/1966 |
| GB | 1367490 | A | 9/1974 |
| GB | 1578461 | A | 11/1980 |
| JP | S58146345 | A | 8/1983 |
| JP | S60203264 | A | 10/1985 |
| JP | H0482974 | A | 3/1992 |
| JP | H04146273 | A | 5/1992 |
| JP | 05184661 | A * | 7/1993 ............. A61L 27/60 |
| JP | H05279966 | A | 10/1993 |
| JP | 6017378 | A | 1/1994 |
| JP | H0617378 | A | 1/1994 |
| JP | H06158546 | A | 6/1994 |
| JP | H06198800 | A | 7/1994 |
| JP | H0770600 | A | 3/1995 |
| JP | 9047502 | A | 2/1997 |
| JP | 3184405 | U | 6/2013 |
| KR | 100716015 | B1 | 5/2007 |
| KR | 20110133893 | A | 12/2011 |
| RU | 2235744 | C2 | 9/2004 |
| RU | 2575263 | C2 | 2/2016 |
| RU | 2617360 | C2 | 4/2017 |
| WO | WO-8303224 | A1 | 9/1983 |
| WO | WO-9119806 | A1 | 12/1991 |
| WO | WO-9412563 | A1 | 6/1994 |
| WO | WO 96/01912 | | 1/1996 |
| WO | WO-9717459 | A1 | 5/1997 |
| WO | WO-9730582 | A1 | 8/1997 |
| WO | WO-9748814 | A2 | 12/1997 |
| WO | WO-9808962 | A1 | 3/1998 |
| WO | WO-9831812 | A1 | 7/1998 |
| WO | WO-9845457 | A1 | 10/1998 |
| WO | WO-9858069 | A1 | 12/1998 |
| WO | WO-9907206 | A1 | 2/1999 |
| WO | WO-9916890 | A2 | 4/1999 |
| WO | WO-9931222 | A1 | 6/1999 |
| WO | WO-9931223 | A1 | 6/1999 |
| WO | WO-9931248 | A1 | 6/1999 |
| WO | WO-9940210 | A1 | 8/1999 |
| WO | 1305546 | A | 7/2001 |
| WO | WO-0160922 | A1 | 8/2001 |
| WO | WO-0168811 | A2 | 9/2001 |
| WO | WO-2005081970 | A2 | 9/2005 |
| WO | WO-2007124023 | A2 | 11/2007 |
| WO | WO-2009066635 | A1 | 5/2009 |
| WO | WO-2009070720 | A1 | 6/2009 |
| WO | WO-2009149181 | A2 | 12/2009 |
| WO | WO-2010008905 | A2 | 1/2010 |
| WO | WO-2010021738 | A2 | 2/2010 |
| WO | WO-2010048281 | A1 | 4/2010 |
| WO | WO-2010091251 | A2 | 8/2010 |
| WO | WO-2011051983 | A1 | 5/2011 |
| WO | WO-2012054195 | A2 | 4/2012 |
| WO | WO-2012108907 | A1 | 8/2012 |
| WO | WO-2013039118 | A1 | 3/2013 |
| WO | WO-2013072063 | A1 | 5/2013 |
| WO | WO-2013149083 | A1 | 10/2013 |
| WO | WO-2014039938 | A1 | 3/2014 |
| WO | 2014/195426 | A1 | 12/2014 |
| WO | WO 2014/201406 | | 12/2014 |
| WO | WO-2016073453 | A1 | 5/2016 |
| WO | WO-2017053433 | A1 | 3/2017 |
| WO | WO-2017131196 | A1 | 8/2017 |
| WO | WO-2017142892 | A1 | 8/2017 |

OTHER PUBLICATIONS

International Search Report and Written Opinion dated Dec. 15, 2016 in PCT/US2016/052891 filed Sep. 21, 2016.
Extended European Search Report dated Jul. 5, 2019 in European Patent Application No. 16849509.1, 4 pages.
Abedin, M.Z., et al., "Isolation and Native Characterization of Cysteine-rich Collagens From Bovine Placental Tissues and Uterus and Their Relationship to Types Iv and V Collagens," Bioscience Reports, 2(7):493-502, Portland Press on behalf of the Biochemical Society, England, (Jul. 1982).
Aldhous, Print me a heart and a set of arteries, New Scientist, Apr. 15, 2006, retrieved from the internet on Jun. 3, 2015. Retrieved from the Internet: (http://organprint.missouri.edu/www/news/NewScientistApril2006.pdf).
Apte, S.S., et al., "Cloning of the Human and Mouse Type X Collagen Genes and Mapping of the Mouse Type X Collagen Gene to Chromosome 10," European Journal of Biochemistry, 206(1):217-224, Blackwell Science Ltd. on behalf of the Federation of European Biochemical Societies, England, (May 1992).
Arding, Vegetarian cheese, Culture the word on cheese, 2 pgs, Dec. 3, 2013, retrieved from the internet on Oct. 31, 2014. Retrieved from the Internet: (URL: https://culturecheesemag.com/ask-the-monger/vegetarian-cheese).
Ayad, S., et al., "Bovine Cartilage Types VI and IX Collagens," Biochemical Journal, 262(3):753-761, Published by Portland Press on behalf of the Biochemical Society, England, (Sep. 1989).
Bailey, A.J., et al., "Irradiation-Induced Crosslinking of Collagen," Radiation Research, 22(4):606-621, Kluge Carden Jennings Pub. Co, United States, (Aug. 1964).
Barnard, N.D., et al., "The Medical Costs Attributable to Meat Consumption," Preventive Medicine, 24(6):646-655, Academic Press, Inc (Nov. 1995).
Benjaminson, M.A., et al., "In Vitro Edible Muscle Protein Production System (MPPS): Stage 1, Fish," Acta Astronautica, 51(12):879-889, Pergamon Press, England(Dec. 2002).
Bentz, H., et al., "Isolation and Partial Characterization of a New Collagen With an Extended Triple-helical Structural Domain," Proceedings of the National Academy of Sciences of the United States of America, 80(11):3168-3172, National Academy of Sciences, United States, (Jun. 1983).
Benya, P.D and Padilla, S.R, "Isolation and Characterization of Type VIII Collagen Synthesized by Cultured Rabbit Corneal Endothelial Cells," The Journal of Biological Chemistry, 261(9):416-4169, American Society for Biochemistry and Molecular Biology, United States, (Mar. 1986).
Berger, P.H., et al. , "Expression in Transgenic Plants of a Viral Gene Product That Mediates Insect Transmission of Potyviruses," Proceedings of the National Academy of Sciences of the United States of America, 86(21):8402-8406, National Academy of Sciences, United States, (Nov. 1989).
Bevan, M, "The Structure and Transcription Start Site of a Major Potato Tuber Protein Gene," Nucleic Acids Research, 14(11):4625-4638, Information Retrieval ltd, England, (Jun. 1986).

(56) References Cited

OTHER PUBLICATIONS

Bhat, Z.F and Bhat, H., "Animal-free Meat Biofrabrication," American Journal of Food Technology, 6(6):441-459, (Jun. 2011).
Bhat, Z.F and Bhat H., "Tissue Engineered Meat-Future Meat," Journal of Stored Products and Postharvest Research, 2(1):1-10, (Jan. 2011).
Bian, W. and Bursac, N.,, "Engineered Skeletal Muscle Tissue Networks With Controllable Architecture," Biomaterials, 30(7):1401-1412, IPC Science and Technology Press, Netherlands, (Mar. 2009).
Bitter, G.A, "Heterologous Gene Expression in Yeast," Methods in Enzymology 152:673-684, Academic Press, United States (1987).
Boonen, K.J and Post, M.J., "The Muscle Stem Cell Niche: Regulation of Satellite Cells During Regeneration," Tissue Engineering Part B, 14(4):419-431, Mary Ann Liebert, Inc, United States (Dec. 2008).
Boonen K.J.M., et al., "Essential Environmental Cues From the Satellite Cell Niche: Optimizing Proliferation and Differentiation," American Journal of Physiology-Cell Physiology, 296(6):C1338-C1345, (Jun. 2009).
Bray E.A, "Expression of the βsubunit of βconglycinin in Seeds of Transgenic Plants," Planta, 172(3):364-370, Springer-Verlag [etc.], Germany, (Nov. 1987).
Brisson, N., et al., "Plant Virus Vectors: Cauliflower Mosaic Virus," Methods for Plant Molecular Biology, 437-446, New York, Academic Press, (1988).
Brogile, R., et al., "Light-regulated Expression of a Pea Ribulose-1, 5-bisphosphate Carboxylase Small Subunit Gene in Transformed Plant Cells," Science 224(4651):838-843, Nature Publishing Group, England (May 1984).
Burgeson, R.E and Nimni, M.E, "Collagen Types: Molecular Structure and Tissue Distribution," Clinical Orthopaedics and Related Research, 282:250-272, Wolters Kluwer, United States, (Sep. 1992).
Byers, P.H, "Preparation of Type III Procollagen and Collagen From Rat Skin," Biochemistry, 13(25):5243-5248, American Chemical Society, United States, (Dec. 1974).
Casas A.M., et al., "Transgenic Sorghum Plants via Micro Projectile Bombardment," Proceedings of the National Academy of Sciences of the United States of America, 90(23):11212-11216, National Academy of Sciences, United States, (Dec. 1993).
Christensen A.H., et al., "Maize Polyubiquitin Genes: Structure, Thermal Perturbation of Expression and Transcript Splicing, and Promoter Activity Following Transfer to Protoplasts by Electroporation," Plant Molecular Biology, 18(4):675-689, (Feb. 1992).
Christou, P., et al. , "The Development of a Variety-independent Gene-transfer Method for Rice," Trends in Biotechnology, 10:239-246, Elsevier Inc., (Jul. 1992).
Chua, J., "Grow Your Own Microbial 'Leather' in Your Kitchen (DIY Tutorial)", Ecouterre, Feb. 23, 2015, [online], [Retrieved on Sep. 1, 2017], Retrieved from the Internet (URL: www.ecouterre.com/grow-your-own-microbial-leatherin your-kitchen-diy-tutorial).
Cornejo, M.J., et al., "Activity of a Maize Ubiquitin Promoter in Transgenic Rice," Plant Molecular Biology, 23(3):567-581, Kluwer Academic, Netherlands, (Nov. 1993).
Coruzzi, G., et al., "Tissue-specific and Light-regulated Expression of a Pea Nuclear Gene Encoding the Small Subunit of Ribulose-1, 5-Bisphosphate Carboxylase," European Molecular Biology Organization 3(8):1671-1679, PMC, United States National Library of Medicine National Institutes of Health, United States (Aug. 1984).
Database WPI, Week 199427, Thomson Scientific, London, GB, 1994-AN 1994-222702.
Datar, I and Betti, M., "Possibilities for an in Vitro Meat Production System," Innovation Food Science and Emerging Technologies, 11(1):13-22, Elsevier Ltd(Jan. 2010).
De-Deyne, P.G., "Formation of Sarcomeres in Developing Myotubes: Role of Mechanical Stretch and Contractile Activation," American Journal of Physiology-Cell Physiology, 279(6):C1801-C1811, (Dec. 2000).
Dennis, R.G and Kosnik, P.E 2nd., "Excitability and Isometric Contractile Properties of Mammalian Skeletal Muscle Constructs Engineered in Vitro," In Vitro Cellular & Developmental Biology, 36(5):327-335, Springer, Germany (May 2000).
Dennis, R.G., et al., "Excitability and Contractility of Skeletal Muscle Engineered From Primary Cultures and Cell Lines," American Journal of Physiology-Cell Physiology, 280(2):C288-C295, American Physiological Society, United States (Feb. 2001).
Duance, V.C., et al., "Isolation and Characterization of the Precursor of Type M Collagen," Biochemical Journal, 221(3):885-889, Published by Portland Press on behalf of the Biochemical Society, England, (Aug. 1984).
Dublet, B., et al., "The Structure of Avian Type XII Collagen," Journal of Biological Chemistry, 264(22):13150-13156, American Society for Biochemistry and Molecular Biology, United States, (Aug. 1989).
Edelman, E.R. , "Vascular Tissue Engineering: Designer Arteries," Circulation Research 85(12):1115-1117, Lippincott Williams & Wilkins, United States (Dec. 1999).
Edelman, P.D., et al., "Commentary: in Vitro-cultured Meat Production," Tissue Engineering, 11(5-6):659-662, Mary Ann Liebert, Inc, United States (May-Jun. 2005).
Elstow, S.F. and Weiss, J.B, "Extraction, Isolation and Characterization of Neutral Salt Soluble Type V Collagen From Fetal Calf Skin," Collagen and Related Research, 3(3):181-193, Gustav Fischer Verlag, Germany, (May 1983).
Engler, A. J., et al., "Myotubes Differentiate Optimally on Substrate With Tissue-like Stiffness: Pathological Implications for Soft or Stiff Microenvironments," Journal of Cell Biology, 166(6):877-887, Rockefeller University Press, United States (Sep. 2004).
Li, M., et al., "Soy Protein-Modified Waterborne Polyurethane Biocomposites With Improved Functionality", RSC advances, 6(16):12837-12849, Royal Society of Chemistry (Jan. 2016).
Chen, Y., et al., "Structure and Properties of Composites Compression-Molded from Polyurethane Prepolymer and Various Soy Products", Industrial & Engineering Chemistry Research, 42(26):6786-6794, American Chemical Society (Dec. 2003).
Zhang, M., et al., "Development of Soy Protein Isolate/waterborne Polyurethane Blend Films With Improved Properties," Colloids and Surfaces B: Biointerfaces 100:16-21, Elsevier B.V, Netherlands (Dec. 2012).
Fonseca, S., et al., "Slow Fiber Cluster Pattern in Pig Longissimus Thoracic Muscle: Implications for Myogenesis," Journal of Animal Science, 81(4):973-983, American Society of Animal Science, United States (Apr. 2003).
Foucher, A.E., et al., "Purification and Characterization of Native Type XIV Collagen," The Journal of Biological Chemistry, 267(22):15759-15764, American Society for Biochemistry and Molecular Biology, United States, (Aug. 1992).
Fromm, M.E., et al., "Inheritance and Expression of Chimeric Genes in the Progeny of Transgenic Maize Plants," Bio/technology (Nature Publishing Company), 8(9):833-839, Nature Publishing Company, [c1983]-1996, United States, (Sep. 1990).
Future Trends in the World Leather Products Industry and Trade, United Nation Industrial Development Organization, Vienna, 2010.
Gawlitta, D., et al., "The Influence of Serum-free Culture Conditions on Skeletal Muscle Differentiation in a Tissue-engineered Model," Tissue Engineering Part A, 14(1):161-171, (Jan. 2008).
Gordon, et al., "Discovery of a New Collagen, Type XX, Present in Chick Cornea," Investigative Ophthalmology & Visual Science, 39(4):S1128, (Mar. 1998), Abstract only).
Gordon, et al., "Type XX Collagen, A New Member of the Fribil-Associated (FACIT) Family of Collagens," The FASEB Journal, 13(5):A1119, (Mar. 1999).
Gurley, W.B., et al., "Upstream Sequences Required for Efficient Expression of a Soybean Heat Shock Gene," Molecular and Cellular Biology 6(2):559-565, American Society for Microbiology, United States (Feb. 1986).
Harris, J.R., et al., "In Vitro Fibrillogenesis of Collagen Type I in Varying Ionic and Ph Conditions," Micron, 49:60-68, Pergamon Press, c1993 , England, (Jun. 2013).
Hinchee, M.A.W., et al., "Production of Transgenic Soybean Plants Using Agrobacterium-mediated DNA Transfer," Bio/Technology, 6:915-922, (Aug. 1988).

(56) References Cited

OTHER PUBLICATIONS

Hopkins, P.D and Dacey, A., Vegetarian meat: could technology save animals and satify meat eaters?, Journal of Agricultural and Environmental Ethics, 21(6):579-596, Springer, 2008, retrieved from the internet on Jun. 2, 2015 (http://foodethics.univie.ac.at/fileadmin/user.sub.--upload/inst.sub.---et- hik.sub.--dialog/Hopkins.sub.--P..sub.--2008.sub.--Veg.sub.--Me- at.sub.--and.sub.--In.sub.--Meat.pdf.

Housley, T., et al., "Collagen Crosslinking: Isolation of Hydroxyaldoi-histidine, a Naturally-occurring Crosslink," Biochemical and Biophysical Research Communications, 67(2):824-830, (Dec. 1975).

Huebner, K., et al., "Chromosomal Assignment of a Gene Encoding a New Collagen Type (Col 15a1) to 9q21-7 Q22," Genomics, 14(2):220-224, Academic Press, [c1987, United States, (Oct. 1992).

Inoguchi, K, "The mRNA for Alpha 1(Xix) Collagen Chain, a New Member of Facits, Contains a Long Unusual 3' Untranslated Region and Displays Many Unique Splicing Variants.," Journal of Biochemistry, 117(1):137-146, Oxford University Press, England, (Jan. 1995).

Inouye, S., et al., "Up-Promoter Mutations in the Ipp Gene of *Escherichia coli*," Nucleic Acids Research 13(9):3101-3110, Oxford University Press, Enlgand (1985).

International Search Report and Written Opinion for International Application No. PCT/US2016/052891, dated Dec. 15, 2016.

Xie, D.Y., et al., "Roles of Soft Segment Length in Structure and Property of Soy Protein Isolate/Waterbourne Polyurethane Blend Films," Journal of Industrial and Engineering Chemistry Research 55(5):1229-1235, American Chemical Society (Jan. 2016).

Wang, N., et al., "Mechanical Properties and Biodegradability of Crosslinked Soy Protein Isolate/Waterborne Polyurethane Composites," Journal of Applied Polymer Science 95:465-473, Wiley Periodicals, Inc (2005).

Wang, N and Zhang, L., "Preparation and characterization of soy protein plastics plasticized with waterborne polyurethane," Polymer International 54(1):233-239, Society of Chemical Industry, (Jan. 2005).

Tong, X., et al., "Development of blend films from soy meal protein and crude glycerol-based waterborne polyurethane," Industrial Crops and Products 67:11-17, Elsevier B.V (May 2015).

Wang, G and Zhou, A., "Soy Protein Based Biodegradable Flexible Polyurethane Foam," Advanced Materials Research, 152-153:1862-1865, Trans Tech Publication, Switzerland (2011).

Jakab, K., et al., "Engineering Biological Structures of Prescribed Shape Using Self-assembling Multicellular Systems," Proceedings of the National Academy of Sciences of the United States of America 101(9):2864-2869, National Academy of Sciences, United States (Mar. 2004).

Jakab, K., et al., "Tissue Engineering by Self-assembly and Bioprinting of Living Cells," Biofabrication 2(2):022001, IOP Publishing, England (Jun. 2010).

Jenkins, C.L., et al., "Effect of 3-hydroxyproline Residues on Collagen Stability," Journal of the American Chemical Society, 125(21):6422-6427, American Chemical Society, United States, (May 2003).

Jones, B.M.M., et al., "Collagen Fibril Orientation in Ovine and Bovine Leather Affects Strength: A Small Angle X-ray Scattering (SAXS) Study," Journal of Agricultural and Food Chemistry, 59(18):9972-9979, American Chemical Society, United States, (Sep. 2011).

Juvonen, M., et al., "Patterns of Expression of the Six Alternatively Spliced Exons Affecting the Structures of the COL 1 and NC2 Domains of the a1 (XIII) Collagen Chain in Human Tissues and Cells Lines," The Journal of Biological Chemistry, 267 (34):24700-24707, (Dec. 1992).

Kapoor, R, "Type VIII Collagen From Bovine Descemet's Membrane: Structural Characterization of a Triple-helical Domain," Biochemistry, 25(13):3930-3937, American Chemical Society, United States, (Jul. 1986).

Katsumata, M., "Promotion of Intramuscular Fat Accumulation in Porcine Muscle by Nutritional Regulation," Animal Science Journal, 82(1):17-25, Wiley, Australia (Feb. 2011).

Kay, R., et al., "Duplication of Camv 35S Promoter Sequences Creates a Strong Enhancer for Plant Genes," Science, 236(4806):1299-1302, American Association for the Advancement of Science, United States, (Jun. 1987).

Kielty, C.M., et al., "Isolation and Ultrastructural Analysis of Microfibrillar Structures From Foetal Bovine Elastic Tissues," Journal of cell science, 99(4):797-807, Company of Biologist, England, (Aug. 1991).

Kielty, C.M., et al, "The Collagen Family: Structure, Assembly and Organization in the Extracellular Matrix," Connective Tissue and Its Heritable Disorders: Molecular, Genetic, and Medical Aspects, 159-221, (2002).

Kivirikko, S., et al., "Primary Structure of the Alpha 1 Chain of Human Type Xv Collagen and Exon-intron Organization in the 3'Region of the Corresponding Gene," The Journal of biological chemistry, 269(7):4773-4779, American Society for Biochemistry and Molecular Biology, (Feb. 1994).

Klemm, D., et al., "Cellulose: Fascinating Biopolymer and Sustainable Raw Material," Angewandte Chemie International Edition, 44(22):3358-3393, (May 2005).

Kosnik, P.E., et al., "Tissue Engineering Skeletal Muscle," Functional Tissue Engineering, 377-392, Springer-Verlag, United States, (2003).

Langelaan M.L.P., et al., "Meet the New Meat: Tissue Engineered Skeletal Muscle," Trends in Food Science & Technology, 21(2):59-66, Elsevier, (Feb. 2010).

Langer, R. and Vacanti, J.P., "Tissue Engineering; Science," Science, 260(5110):920-926, American Association for the Advancement of Science, (May 1993).

Lanza., et al., "Principles of Tissue Engineering; 3rd. Ed.; Chapter 12 Principles of Tissue Culture and Bioreactor Design (III. Principle of Bioreactor Design)," Academic Press, 165-166, (Aug. 2007).

Lee, N., et al., "Efficient Transformation and Regeneration of Rice Small Cell Groups," Proceedings of the National Academy Sciences of the United States of America, 88(15):6389-6393, National Academy of Sciences, United States, (Aug. 1991).

Lee, W., et al., "Multi-layered Culture of Human Skin Fibroblast and Keratinocytes Through Three-dimensional Freeform Fabrication," Biomaterials 30(8):1587-1595, Elsevier Science, Netherlands (Mar. 2009).

Levenberg, S., et al., "Engineering Vascularized Skeletal Muscle Tissue," Nature Biotechnology, 23(7):879-884, Nature America Publishing, United States (Jul. 2005).

Li, K., et al., "Cloning of Type XVII Collagen," The Journal of biological chemistry, 268(12):8825-8834, American Society for Biochemistry and Molecular Biology, United States, (Apr. 1993).

Li, M., et al., "Electrospun Protein Fibers as Matrices for Tissue Engineering," Biomaterials, 26(30):5999-6008, IPC Science and Technology Press, Netherlands, (Oct. 2005).

Logan, J., et al., "Adenovirus Tripartite Leader Sequence Enhances Translation of mRNAs Late After Infection," Proceedings of the National Academy of Sciences USA 81(12):3655-3659, National Academy of Sciences, United States (Jun. 1984).

Lucklow, V.A., et al., "High Level Expression of Nonfused Foreign Genes With Autographa Californica Nuclear Polyhedrosis Virus Expression Virus Expression Vectors," Virology 170(1):31-39 (May 1989).

Lunstrum, G.P., et al., "Identification and Partial Purification of a Large, Variant Form of Type XII Collagen," The Journal of biological chemistry, 267(28):20087-20092, American Society for Biochemistry and Molecular Biology, United States, (Oct. 1992).

Lunstrum, G.P., et al., "Large Complex Globular Doamins of Type Vii Procollagen Contribute to the Structure of Anchoring Fibrils," The Journal of biological chemistry, 261(19):9042-9048, American Society for Biochemistry and Molecular Biology, United States, (Jul. 1986).

Mackett, M., et al., "General Method for Production and Selection of Infectious Vaccinia Virus Recombinants Expressing Foreign Genes," Journal of Virology 49(3):857-864, American Society for Microbiology, United States (Mar. 1984).

(56) References Cited

OTHER PUBLICATIONS

Mackett, M., et al., "Vaccinia Virus: A Selectable Eukaryotic Cloning and Expression Vector," Proceedings of the National Academy of Sciences USA 79(23):7415-7419, National Academy of Sciences, United States (Dec. 1982).
Marga. F., et al., "Developmental Biology and Tissue Engineering," Birth Defects Research Part C: Embryo Today 81(4):320-328, Wiley Periodicals, Inc, United States (Dec. 2007).
Marga. F., et al., "Toward Engineering Functional Organ Modules by Additive Manufacturing," Biofabrication 4(2):022001, IOP Publishing, England (Jun. 2012).
Matsuda, N., et al., "Tissue Engineering Based on Cell Sheet Technology," Advanced Materials, 19(20):3089-3099, John Wiley & Sons, (Oct. 2007).
McElroy, D., et al., "Isolation of an Efficient Actin Promoter for Use in Rice Transformation," The Plant cell, 2(2):163-171, American Society of Plant Physiologists, c1989, United States, (Feb. 1990).
McGrath, J.A., et al., "Mutations in the 180-kd Bullous Pemphigoid Antigen (Bpag2), a Hemidesmosomal Transmembrane Collagen (Col 17a1), in Generalized Atrophic Benign Epidermolysis Bullosa," Nature genetics, 11(1):83-86, Nature Pub. Co., c1992, United States, (Sep. 1995).
Mead, P.S., et al., "Food-related Illness and Death in the United States," Emerging infectious diseases, 5(5):607-625, National Center for Infectious Diseases, Centers for Disease Control and Prevention (CDC), United States, (Sep. 1999).
Mechanic, G. and Tanzer, M.L, "Biochemistry of Collagen Crosslingen Isolation of a New Crosslink, Hydroxylysinohydroxynorleucine, and Its Reduced Precursor, Dihydroxynorleucine, From Bovine Tendon," Biochemical and biophysical research communication, 41(6):1597-1604, Elsevier, United States, (Dec. 1970).
Mechanic, G., et al., "The Nature of Crosslinking in Collagens From Mineralized Tissues," Biochemical and biophysical research communications, 45(3):644-653, Elsevier, United States, (Nov. 1971).
Medberry, S.L., et al., "The Commelina Yellow Mottle Virus Promoter is a Strong Promoter in Vascular and Reproductive Tissue," The Plant cell, 4(2):185-192, American Society of Plant Physiologist, c1989, United States, (Feb. 1992).
Meyer, M., et al., "Collagen Fibres by Theromoplastic and Wet Spinning," Materials Science and Engineering C, 30(8):1266-1271, ResearchGate, (Oct. 2010).
Miller, E.J. and Rhodes, R.K, "[2] Preparation and Characterization of the Different Types of Collagen," Methods in enzymology, 82(A):33-64, Academic Press, United States, (1982).
Mironov., et al., "Biofabrication: a 21st century manufacturing paradigm" Biofabrication 1 (2009) pp. 1-16.
Mironov, V., et al., "Bioprinting Living Structures," Journal of Materials Chemistry 17(20):2054-2060 (May 2007).
Munarin, F., et al., "Pectin-based Injectable Biomaterials for Bone Tissue Engineering," Biomacromolecules, 12(3):568-577, American Chemical Society, United States, (Mar. 2011), (Abstract Only).
Muragaki. Y., et al., "The Human Alpha 1(Xv) Collagen Chain Contains a Large Amino-terminal Non-triple Helical Doamin With a Tandem Repeat Structure and Homology to Alpha 1(Xviii) Collagen," The Journal of biological chemistry, 269(6):4042-4046, American Society for Biochemistry and Molecular Biology, United States, (Feb. 1994).
Myers, J.C., et al., "Identification of a Previously Unknown Human Collagen Chain, Alpha 1(Xv), Characterized by Extensive Interruptions in the Triple-helical Region," Proceedings of the National Academy of Sciences of the United States of America, 89(21):10144-10148, National Academy of Sciences, United States, (Nov. 1992).
Meyers, J.C., et al., "The Triple-helical Region of Human Type Xix Collagen Consists of Multiple Collagenous Subdomains and Exhibits Limited Sequence Homology to Alpha 1(XVI)," The Journal of biological chemistry, 269(28):18549-18557, American Society for Biochemistry and Molecular Biology, United States, (Jul. 1994).
Park, S.K., et al., "Physical and Mechanical Soy Protein-Based Plastic Foams," Journal of the American Oil Chemists Society 76(10):1201-1205, AOCS Press, United States (1999).

Niklason, L.E., et al., "Advances in Tissue Engineering of Blood Vessels and Other Tissues," Transplant Immunology 5(4):303-306, Elsevier, Netherlands (Dec. 1997).
Norotte, C., et al., "Scaffold-free Vascular Tissue Engineering Using Bioprinting," Biomaterials 30(30):5910-5917, Elsevier Science, Netherlands (Oct. 2009).
Oh, S.P., et al., "Cloning of Cdna and Genomic Dna Encoding Human Type XVIII Collagen and Localization of the Alpha 1(XVIII) Collagen Gene to Mouse Chromosome 10 and Human Chromosomes 21," Genomics, 19(3):494-499, Academic Press, [c1987, United States, (Feb. 1994).
Oh, S.P., et al., "Isolation and Sequencing of cDNAs for Proteins With Multiple Domains of Gly-xaa-yaa Repeats Identify a Distint Family of Collagenous Proteins," Proceedings of the National Academy of Sciences of the United States of America, 91(10):4229-4233, National Academy of Sciences, United States, (May 1994).
Olkkonen, V.M., et al., "Expression of Exogenous Proteins in Mammalian Cells With the Semliki Forest Virus Vector," Methods in cell biology, 43(A):43-53, Academic Press, United States, (1994).
Pan, T.C., et al., "Cloning and Chromosomal Location of Human Alpha 1(XVI) Collagen," Proceedings of the National Academy of Sciences of the United States of America, 89(14):6565-6569, National Academy of Sciences, United States, (Jul. 1992).
Panicali, D., et al., "Construction of Poxviruses as Cloning Vectors: Insertion of the Thymidine Kinase Gene Herpes Simplex virus into the DNA of Infectious Vaccinia Virus," Proceedings of the National Academy of Sciences USA 79(16):4927-4931, The National Academy of Sciences of the United States (Aug. 1982).
Park, H., et al.,, "Effects of Electrical Stimulation in C2C12 Muscle Constructs," Journal of tissue engineering and regenerative medicine, 2(5):279-287, John Wiley & Sons, England, (Jul. 2008).
Paszkowski, J., et al., "Direct Gene Transfer to Plants," The EMBO journal, 3(12):2717-2722, Wiley Blackwell, England, (Dec. 1984).
Pedersen, K., et al., "Cloning and Sequence Analysis Reveal Structural Variation Among Related Zein Genes in Maize," Cell, 29(3):1015-1026, Cell Press, United States, (Jul. 1982).
Perera, G., et al., "Hydrophobic Thiolation of Pectin With 4-aminothiophenol: Synthesis and in Vito Characterization," American Association of Pharaceutical Scientist, 11(1):174-180, American Association of Pharmaceutical Scientist, United States, (Mar. 2010).
Perez-Pomares, J.M., et al., "Tissue Fusion and Cell Sorting in Embryonic Development and Diease: Biomedical Implications," Bioessays 28(8):809-821, Wiley, United States (Aug. 2006).
Pette D., et al., "What Does Chronic Electrical Stimulation Teach Us About Muscle Plasticity?," Muscle & Nerve, 22(6):666-677, John Wiley & Sons, United States (Jun. 1999).
Prockop, D.J. and Kivirikko, K.I. "Collagens: Molecular Biology, Diseases, and Potentials for Therapy," Annual review of biochemistry, 64:403-434, Annaul Reviews, United States (1995).
Suganya, S., et al., "Naturally Derived Biofunctional Nanofibrous Scaffold For Skin Tissue Regeneration," International Journal of Biological Macromolecules 68:135-143, Elsevier, Netherlands (Jul. 2014).
Rehn, M. and Pihlajaniemi, T, "Alpha 1 (XVIII), a Collagen Chain With Frequent Interruptions in the Collagenous Sequence, a Distinct Tissue Disrtibution, and Homology With Type XV Collagen," Proceedings of the National Academy of Sciences of the United States of America, 91(10):4234-4238, National Academy of Sciences, United States, (May 1994).
Rehn, M., et al., "Primary Structure of the Alpha 1 Chain of Mouse Type Xviii Collagen, Partial Structure of the Corresponding Gene, and Comparison of the Alpha 1(Xviii) Chain With Its Homologue, the Alpha 1(Xv) Collagen Chain," The Journal of biological chemistry, 269(19):13929-13935, American Society for Biochemistry and Molecular Biology, United States, (May 1994).
Riggs, C.D. and Bates, G.W, "The Stable Transformation of Tobacco by Electroporation: Evidence for Plasmid Concatenation," Proceedings of the National Academy of Sciences of the United States of America, 83(15):5602-5606, National Academy of Sciences, United States, (Aug. 1986).
Rober, M.B.T. et al., "One of Two Different ADP-glucose Pyrophosphorylase Genes From Potato Responds Strongly to Elevated

(56) References Cited

OTHER PUBLICATIONS

Levels of Sucrose," Molecular & general genetics, 224(1):136-146, New York Springer-Verlag [1967, Germany, (Oct. 1990).
Rogers, J.C., "Two Barley Alpha-amylase Gene Families Are Regulated Differently in Aleurone Cells," The Journal of biological chemistry, 260(6):3731-3738, American Society for Biochemistry and Molecular Biology, United States, (Mar. 1985).
Rogers, S.G., et al., "Improved Vectors for Plant Transformation: Expression Cassette Vectors and New Selectable Markers," Methods in enzymology, 153:253-277, Elsevier Inc, (1987).
Ruther, U. and Muller-Hill, B., "Easy Identification of cDNA Clones," The EMBO Journal 2(10):1791-1794, IRL Press Ltd, England (1983).
Sanger, M., et al., "Characterization of Strong Promoter From Figwort Mosaic Virus: Comparison With the Analogous 35s Promoter From Cauliflower Mosaic Virus and the Regulated Mannopine Synthase Promoter," Plant molecular biology, 14(3):433-443, Martinus Nijhoff/Dr. W. Junk, 1981, Netherlands, (Mar. 1990).
Savadogo, P., et al.,, "Effects of Grazing Intensity and Prescribed fire on Soil Physical and Hydrological Properties and Pasture Yield in the Savanna Woodlands of Burkina Faso," Agriculture, Ecosystems & Environments, 118(1-4):80-92, Elsevier B.V., (Jan. 2007).
Schardl, C.L., et al., "Design and Construction of a Versatile System for the Expression of Foreign Genes in Plants," Gene, 61(1):1-11, Elsevier/North-Holland, 1976, Netherlands, (1987).
Schmitt, F.O., et al., "Electron Microscope Investigations of the Structure of Collagen," Journal of Cellular Physiology, 20(1):11-33, (Aug. 1942).
Sekine, H., et al., "Myocardial Tissue Reconstruction: the Cell Sheet Engineering Approach," Inflammation and Regeneration, 27 (3):171-176, (May 2007).
Shayegan, M. and Forde, N.F.,, "Microrheological Characterization of Collagen Systems: From Molecular Solutions to Fibrillar Gels," PloS one, 8(8):1-12, Public Library of Science, United States, (Aug. 2013).
Shepherd, J.H., et al., "Effect of Fiber Crosslinking on Collagen-fiber Reinforced Collagen-chondroitin-6-sulfate Materials for Regenerating Load-bearing Soft Tissues," Journal of biomedical materials research. Part A, 101(1):176-184, john Wiley & Sons, United States, (Jan. 2013).
Shoshan, S. and Finkelstein, S., "Studies on Collagen Crosslinking in Vivo," Biochimica et biophysica acta, 154(1):261-263, Elsevier Pub. Co., Netherlands, (Jan. 1968).
Siegel, R.C., "Biosynthesis of collagen Crosslinks: Increased Activity of Purified Lysyl Oxidase With Reconstituted Collagen Fibrils," Proceedings of the National Academy of Sciences of the United States of America, 71(12):4826-4830, National Academy of Sciences, United States, (Dec. 1974).
Silva, T.H., et al., "Marine Origin Collagens and Its Potential Applications," Marine drugs, 12(12):5881-5901, MDPI, [2003], Switzerland, (Dec. 2014).
Sizeland, K.H., et al., "Collagen Orientation and Leather Strength for Selected Mammals," Journal of agricultural and food chemistry, 61(4):887-892, American Chemical Society, United States, (Jan. 2013).
Smith, C.M., et al., "Three-dimensional Bioassembly Tool for Generating Viable Tissue-engineered Constructs," Tissue Engineering 10(9-10):1556-1576, Mary Ann Liebert, Inc, United States (Sep.-Oct. 2004).
Smith, G.E., et al., "Molecular Engineering of the Autographa Californica Nuclear Polyhedrosis Virus Genome: Deletion Mutations Within the Polyhedrin Gene," Journal of virology, 46(2):584-593, American Society For Microbiology, United States, (May 1983).
Sommer, F., et al., "Ascorbic Acid Modulates Proliferation and Extracellular Matrix Accumulation of Hyalocytes," Tissue engineering, 13(6):1281-1289, Mary Ann Liebert, Inc., United States, (Jun. 2007) abstract only.
Takamatsu, N., et al., "Expression of Bacterial Chloramphenicol Acetyltransferase Gene in Tobacco Plants Mediated by TMV-RNA," European Molecular Biology Organization Journal 6(2):307-311, IRL Press Limited, Oxford, England, (Feb. 1987).
Teja, A.S and Koh, P.Y, "Synthesis Properties, and Applications of Magnetic Iron Oxide Nanoparticles," Progress in Crystal Growth and Charcterization of Materials, 55(1-2):22-45, (Mar.-Jun. 2009).
Thelen, M.H., et al., "Electrical Stimulation of C2C12 Myotubes Induces Contractions and Represses Thyroid Hormone-Dependent Transcription of the Fast-type Sarcoplasmic-reticulum Ca2+-ATPASE Gene," The Biochemical journal, 321(Pt 3):845-848, Published by Portland Press on behalf of the Biochemical Society, England, (Feb. 1997).
Thibault, J.F., and Rinaudo, M., "Chain Association of Pectic Molecules During Calcium-induced Gelation," Biopolymers, 25(3):455-468, John Wiley & Sons, (Mar. 1986).
Tuomisto H.L. et al., "Environmental Impacts of Cultured Meat Production," Environmental Science & Technolgy, 45(14):6117-6123, American Chemical Society, (Jun. 2011).
Van Heeke, G., et al., "Expression of Human Asparagine Synthetase in *Escherichia coli*," The Journal of Biological Chemistry 264(10):5503-5509, American Society for Biochemistry and Molecular Biology, United States (Apr. 1989).
Wan, Y and Lemaux, P.G., "Generation of Large Numbers of Independently Transformed Fertile Barley Plants," Plant physiology, 104(1):37-48, American Society of Plant Biologist, United States, (Jan. 1994).
Watt, S.L., et al., "Charcterization of Collagen Types Xii and XIV From Fetal Bovine Cartilage," The Journal of biological chemistry, 267(28):20093-20099, American Society for Biochemistry and Molecular Biology, United States, (Oct. 1992).
Wells, H.C., et al., "Collagen Fibril Diameter and Leather Strength," Journal of agricultural and food chemistry, 64(47):11524-11531, American Chemical Society, United States, (Nov. 2013).
Wu, J.J., et al., "Type VI Collagen of the Intervertebral Disc," The Biochemical journal, 248(2):373-281, Published by Portland Press on behalf of the Biochemical Society, England, (Dec. 1987).
Wu, S., et al., "Quantitative Analysis on Collagen Morphology in Aging Skin Based on Multiphoton Microscopy," Journal of biomedical optics, 16(4):40502, SPIE—the International Society for Optical Engineering in cooperation with International Biomedical Optics Society, c1996, (Apr. 2011).
Wu, Y., et al., "Fiber Formation by Dehydration-induced Aggregation of Albumin," Journal of Applied Polymer Science, 129(6):3591-3600, Wiley Periodicals, (Sep. 2013).
Yamaguchi, N., et al., "Molecular Cloning and Partial Characterization of a Novel Collagen Chain, Alpha 1(XVI), Consisting of Repetitive Collagenous Domains and Cysteine-containing Non-Collagenous Segments," Journal of biochemistry, 112(6):856-863, Oxford University Press, England, (Dec. 1992).
Yang, J. et al., "Cell Sheet Engineering: Recreating Tissues Without Biodegradable Scaffolds," Biomaterials, 26(33):6415-6422, Elsevier Science, Netherlands, (Nov. 2005).
Yin, Y. and Beachy, R.N. "The Regulatory Regions of the Rice Tungro Bacilliform Virus Promoter and Interacting Nuclear Factors in Rice (*Oryza Sativa* L.)," The Plant journal : for cell and molecular biology, 7(6):969-980, Blackwell Scientific Publishers and BIOS Scientific Publishers in association with the Society for Experimental Biology, c1991, England, (Jun. 1995).
Yoshioka et al., "Synteny between the Loci for a Novel FACIT-like Collagen Locus (D6S228E) and a1 (IX) Collagen (COL9A1) on 6q12-q14 in Humans," Genomics, 13(3):884-886, Academic Press, United States (Jul. 1992).
Chang, L.C.,et al., "Comparative Study of Physical Properties of Water[Blown Rigid Polyurethane Foams Extended With Commercial Soy Flour ," Journal of Applied Polymer Science 80:10-19, John Wiley & Sons, Inc (2001).
Madbouly, S.A and Lendlein, A., "Degradable Polyurethane/Soy Protein Shape-Memory Polymer Blends Prepared Via Environmentally-Friendly Aqueous Dispersion," Macromolecular Materials and Engineering 297(12):1213-1224,Wiley-VCH Verlag GmbH & Co. KGaA, Weinheim (Nov. 2012).
Halim, A.S., et al., "Biologic and Synthetic Skin Substitutes: An Overview," Indian Journal of Plastic Surgery 43(Suppl): S23-S28, Thieme, Germany (Sep. 2010).

(56) References Cited

OTHER PUBLICATIONS

Huafeng, T., et al., "Improved Flexibility and Water Resistance of Soy Protein Thermoplastics Containing Waterbourne Polyurethane," Industrial Crops and Products 32(1):13-20, Elsevier B.V, (Jul. 2010).
Lin, Y., et al., "Physical, Mechanical, and Thermal Properties of Water-Blown Rigid Polyurethane Foam Containing Soy Protein Isolate," Cereal Chemisty 73(2):189-196, American Association of Cereal Chemists, Inc. (1996).
Lin, Y., et al., "Water[Blown Flexible Polyrethane Foam Extended with Biomass Materials," Journal of Applied Polymer Science 65(4):695-703, John Wiley & Sons, Inc (Jul. 1997).
Liu, D., et al., "Structure and Properties of Blend Films Prepared from Castor Oil-Based Polyurethane/Soy Protein Derivative ," Industrial & Engineering Chemistry Research47(23):9330-9336, American Chemical Society,(2008).
Co-Pending U.S. Appl. No. 16/898,225, filed Jun. 10, 2020, inventor Marga, et al. (Unpublished).
Co-Pending U.S. Appl. No. 16/801,032, filed Feb. 25, 2020, inventor Forgacs, et al. (Unpublished).
Co-Pending U.S. Appl. No. 16/724,689, filed Dec. 23, 2019, inventor Lee, et al. (Unpublished).
Co-Pending U.S. Appl. No. 16/673,603, filed Nov. 4, 2019 , inventor Purcell, et al. (Unpublished).
Co-Pending U.S. Appl. No. 16/744,997, filed Jan. 16, 2020, inventor Teglia, et al. (Unpublished).
Mandal, B, and Majumdar, S.G.,"Nutritional Evaluation of Proteins from three Non-Traditional Seeds with or without Amino Acids Supplementation in Albino Rats," Proceedings of the Indian National Science Academy B50 No. 1:48-56, Nutritional Evaluation of Non-traditional Seed Proteins, Biochemistry Department, Burdwan Medical College, Burdwan (1984).
Rahman, M.M and Netravali, A.N., "Green Resinfrom Forestry Waste Residue "Karanja (*Pongamia pinnata*) Seed Cake" for BiobasedComposite Structures," ACS Sustainable Chemistry & Engineering 2(10):2318-2328, American Chemical Society (Oct. 2014).
Ren, X., et al., "Engineering ZonalCartilage Through Bioprinting Collagen Type II Hydrogel Constructs WithBiomimetic Chondrocyte Density Gradient,"Bmc Musculoskeletal Disorders17: 301, BioMed Central, England (2016).
Wu, B., et al., "The New Development of Modified Collagen Protein Spinning," Leather Science and Engineering 17(4):27-31, China Academic Journal Electronic Publishing House (Aug. 2007).
Co-Pending U.S. Appl. No. 17/260,756, inventor Schachtschneider, S., et al., filed Jul. 15, 2021 (Unpublished).
Co-Pending U.S. Appl. No. 16/978,545 , inventor Babin, N.J., et al., filed Sep. 4, 2020 (Unpublished).
The Editorial Board of Patent Literature Bulletin—Textile, Patent Literature Bulletin—Textile, Shanghai: Shanghai Science and Technology Literature Publishing House, Jun. 30, 1981.
Zang et al., Effects of Collagen Treatment on the Structure and Properties of Salt-Shrinked Filaments, Jiangsu Textile, No. 12, Dec. 31, 2008.
Hu et al., Study on the $Ca(NO_3)2$ Modified Silk Fiber Treated with Chitosan, Silk Research and Technology, China Academic Journal Electronic Publishing House, Dec. 25, 2005.
Chen et al., Study on the Process of Calcium Nitrate Modifying of Mulberry Silk Knitted Fabrics, Journal of Textile Research, vol. 29, No. 1, China Academic Journal Electronic Publishing House, Jan. 15, 2008.
Co-pending U.S. Appl. No. 17/783,570. Inventor: Cai; Shaobo. (Not Published).
Co-pending U.S. Appl. No. 17/819,544 inventor Broadbent; Samuel (Not Published).
Covington, A.D ., "Modern Tanning Chemistry," Chemical Society Reviews, 26: 111-126. (1997).
Jus, S., et al., "Tyrosinase-Catalysed Coating of Wool Fibres With Different Protein-Based Biomaterials," Journal of Biomaterials Science 20(2):253-269, Taylor and Francis, England (2009).
Rajan, R., et al., "Design and in Vitro Evaluation of Chlorpheniramine Maleate From Different Eudragit Based Matrix Patches: Effect of Platicizer and Chemical Enhancers," ARS Pharmaceutica 50(4):177-194 (2010).
Schoff, C.K., "Crosslinking and Crosslink Density," Coatings Clinic (Sep. 1, 2010).
Wang, N., et al., "Properties of Crosslinked Casein/Waterborne Polyurethane Composites," Journal of Applied Polymer Science 91:332-338, John Wiley & Sons, United States (2004).
Yeelack, W and Meesane, J., "Preparation and Characterization of Coated Silk Fibroin Films with Mimicked Re-self Assembly Type I Collagen," The 2013 Biomedical Engineering International Conference, National Research University, Russia (2013).
Yunhui, X.U., et al., "Study of Cotton Fiber Coated by Collagen," Journal of Textile Research 28(5) (May 2007).
Koide, T., "Application of Collagen-like Triple-helical Peptides to Biochemical Studies Elucidating the Collagen Structure and Functions," Seikagaku. The Journal of Japanese Biochemical Society 82(6):474-483, Nippon Seikagakkai, Japan (Jun. 2010).
Langrock, T., et al., "Analysis of Hydroxyproline Isomers and Hydroxylysine by Reversed-Phase HPLC and Mass Spectrometry," Journal of Chromatography B 847(2):282-288, Elsevier, Netherlands (Mar. 2007).
Li, Z., et al., "Mechanical Behaviour of Natural Cow Leather in Tension," Acta Mechanica Solida Sinica 22(1):37-44, AMSS Press, China (2009).
Bareil et al. Collagen Based Biomaterials for Tissue Engineering Applications, Materials, 2010, 3, 1863-1887.
Dascalu, M.C., et al., "On the Compatibility of Low Density Polyethylene/Hydrolyzed Collagen Blends. II: New Compatibilizers," European Polymer Journal 41(6): 1391-1402, Elsevier, Netherlands (2005).

\* cited by examiner

FIBER REINFORCED TISSUE COMPOSITES

CROSS REFERENCE TO RELATED APPLICATIONS

This patent application claims priority to U.S. provisional patent application No. 62/221,521, titled "FIBER REINFORCED TISSUE COMPOSITES" and filed on Sep. 21, 2015, which is herein incorporated by reference in its entirety.

This application may be related to U.S. patent application Ser. No. 15/233,802, titled "ENGINEERED LEATHER AND METHODS OF MANUFACTURE THEREOF" and filed on Aug. 10, 2016 which claimed priority to Ser. No. 13/853,001, filed on Mar. 28, 2013 (titled "ENGINEERED LEATHER AND METHODS OF MANUFACTURE THEREOF"), published as US-2013-0255003. This application may also be related to International Patent Application No. PCT/US2014/042384 ("ENGINEERED LEATHER AND METHODS OF MANUFACTURE THEREOF"), filed on Jun. 13, 2014, and published as WO2014/201406, which claims priority to U.S. Provisional Patent Application No. 61/834,867 filed on Jun. 13, 2013, and titled "ENGINEERED LEATHER AND METHODS OF MANUFACTURE THEREOF". Each of these patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Leather is used in a vast variety of applications, including furniture upholstery, clothing, shoes, luggage, handbag and accessories, and automotive applications. Currently, skins of animals are used as raw materials for natural leather. However, skins from livestock pose environmental concerns because raising livestock requires enormous amounts of feed, pastureland, water, and fossil fuel. Livestock also produces significant pollution for the air and waterways. In addition, use of animal skins to produce leather is objectionable to socially conscious individuals. The global leather industry slaughters more than a billion animals per year. Most of the leather comes from countries with no animal welfare laws or have laws that go largely or completely unenforced. Leather produced without killing animals would have tremendous fashion novelty and appeal.

Although synthetic leather was developed to address some of these concerns, it lacks the quality, durability, and prestige of natural leather. Thus far, scientifically sound and industrially feasible processes have not been developed to produce natural leather. Accordingly, there is a need for a solution to demands for alternative to leather produced from live animals.

Natural leather is typically a durable and flexible material created by the tanning of animal rawhide and skin, often cattle hide. Tanning is generally understood to be the process of treating the skins of animals to produce leather. Tanning may be performed in any number of well-understood ways, including vegetable tanning (e.g., using tannin), chrome tanning (chromium salts including chromium sulfate), aldehyde tanning (using glutaraldehyde or oxazolidine compounds), syntans (synthetic tannins, using aromatic polymers), and the like.

Natural leather is typically prepared in three main parts: preparatory stages, tanning, and crusting. Surface coating may also be included. The preparatory stages prepare the hide/skin for tanning, and unwanted raw skin components are removed. The preparatory stages may include: preservation, soaking (rehydrating), liming, de-hairing, de-fleshing (removing subcutaneous material), splitting, re-liming, deliming (to remove de-hairing and liming chemicals), bating (protein proteolysis), degreasing, frizzing, bleaching, pickling (changing pH), de-pickling, etc.

Tanning is performed to convert proteins in the hide/skin into a stable material that will not putrefy, while allowing the material to remain flexible. Chromium is the most commonly used tanning material. The pH of the skin/hide may be adjusted (e.g., lowered, e.g. to pH 2.8-3.2) to enhance the tanning; following tanning the pH may be raised ("basification" to a slightly higher level, e.g., pH 3.8-4.2).

Crusting refers to the post-tanning treatment that may include coloring (dying), thinning, drying or hydrating, and the like. Examples of crusting techniques include: wetting (rehydrating), sammying (drying), splitting (into thinner layers), shaving, neutralization (adjusting pH to more neutral level), retanning, dyeing, fatliquoring, filling, stuffing, stripping, whitening, fixation of unbound chemicals, setting, conditioning, softening, buffing, etc.

In practice, the process of converting animal skin into leather may include sequential steps such as: unhairing/dehairing, liming, deliming and bateing, pickling, tanning, neutralizing/Dyeing and Fat liquoring, drying and finishing. The dehairing process may chemically remove the hair (e.g., using an alkali solution), while the liming step (e.g., using an alkali and sulfide solution) may further complete the hair removal process and swell ("open up") the collagen. During tanning, the skin structure may be stabilized in the "open" form by replacing some of the collagen with complex ions of chromium. Depending on the compounds used, the color and texture of the leather may change. Tanned leather may be much more flexible than an untreated hide, and also more durable.

Skin, or animal hide, is formed primarily of collagen, a fibrous protein. Collagen is a generic term for a family of at least 28 distinct collagen types; animal skin is typically type 1 collagen (so the term collagen is typically assumed to be type 1 collagen), although other types of collagen may be used in forming leather. Collagens are characterized by a repeating triplet of amino acids, $-(Gly-X-Y)_n-$, so that approximately one-third of the amino acid residues are in collagen are glycine. X is often proline and Y is often hydroxyproline. Thus, the structure of collagen may consist of twined triple units of peptide chains of differing lengths. Different animals may produce different amino acid compositions of the collagen, which may result in different properties (and differences in the resulting leather). Collagen fiber monomers may be produced from alpha-chains of about 1050 amino acids long, so that the triple helix takes the form of a rod of about 300 nm long, with a diameter of 1.5 nm. In the production of extracellular matrix by fibroblast skin cells, triple helix monomers may be synthesized and the monomers may self-assemble into a fibrous form. These triple helices may be held together by salt links, hydrogen bonding, hydrophobic bonding, and covalent bonding. Triple helices can be bound together in bundles called fibrils, and fibril bundles come together to create fibers. Fibers typically divide and join with each other throughout a layer of skin. Variations of the crosslinking or linking may provide strength to the material. Fibers may have a range of diameters. In addition to type I collagen, skin (hides) may include other types of collagen as well, including type III collagen (reticulin), type IV collagen, and type VII collagen.

Previous attempts to make engineered leathers have proven unsuccessful or impractical. For example, EPI 589098 ("the '098 application") describes a method of growing fibroblasts seeded onto three-dimensional bioactive scaffolds. The scaffolds may be made from collagen waste material from a tanning process ("split"), microparticles of pure collagen, particle of collagen waste material, or synthetic scaffolds (e.g., made of polymers such as HYAFF). The addition of the scaffold material complicates and increases the expense of their proposed process, and also affects the properties of any leather produced this way.

The '098 application is one example of a scaffolding technique for culturing leather, however method such as this, which use a scaffold of waste or engineered collagen materials, have not been widely used because they are costly and difficult to work with, and have proven technically difficult to work with and commercialize.

Described herein are engineered leathers that may address the problems by forming materials akin to fiber reinforced composites (FRCs), in which cells are cultured on fibrous scaffolds (formed of fibers such as silk). In general, FRCs refer to composite building materials that form class of high performance materials used in a number of industries including energy, building, automotive, and sport. FRCs consist of a continuous matrix phase (typically a polymer matrix), a dispersed fiber phase (typically a stronger glass, carbon or cellulosic fiber), and an interface between the matrix and fibers. Within the interface, fibers adhere to the matrix phase through covalent or non-covalent interactions for effective force transmission from the matrix phase to the fibers. As a result, materials with incredible strengths can be realized that are not possible with each material individually.

As mentioned, numerous tissue engineering scaffolds have been developed over the past 25 years to build biological tissues with defined structures and dimensions. These scaffolds provide surface area for cells to adhere and grow tissue in three dimensions. Fibrous materials consisting of entangled or woven fibers, 100 nm-100 um in diameter, have been widely explored as tissue engineering scaffolds due to their large surface areas for cell growth per unit volume, and high porosities to allow cell infiltration throughout the 3D scaffold architecture. Typically, tissue engineering scaffolds are biodegradable allowing the tissue to replace the scaffold as it grows. Therefore, the final product consists only of biological tissue to improve biocompatibility following implantation.

Tissue engineering constructs are generally grown for biomedical applications, including insertion into a body to repair and/or replace biological tissue, thus biocompatibility has been an important consideration. However, the use of biological tissues for consumer goods applications requires a much different set of considerations. In such cases, the durability, appearance and ability to be tanned or preserved must be considered. Described herein are methods and techniques for the fabrication of biological tissue, as well as the resulting engineered material, that may address the concerns described above. In particular, described herein are composites wherein the tissue is grown throughout a fibrous scaffold and cross-linked to the scaffold during a process analogous to tanning in order to create a novel class of high performance composites, as well as methods of forming such composites. These engineered leathers may replicate much of the structures and properties of natural leathers, but may be processed in a much simpler manner.

SUMMARY OF THE DISCLOSURE

In general, described herein are engineered, reinforced leather materials (engineered leathers) including a composite of a fibrous scaffold and a collagen network formed by cultured cells (e.g., fibroblasts). These composites are tanned to stabilize the collagen network and interactions between the fibrous scaffold and collagen network. These engineered leathers may be referred to as fiber-reinforced biological tissue composites. Also described herein are methods of making such fiber-reinforced biological tissue composites.

For example, a method of forming a fiber-reinforced biological tissue composite may be formed by culturing tissue-producing cells (e.g., fibroblasts) on a fibrous scaffold having a functional group selected from the group consisting of amine (—NH2), carboxylic acid (—COOH), sulfhydryl (—SH), and hydroxyl (—OH), and combinations thereof, which may be cross-linked (e.g., by tanning) to the tissue and/or proteins, such as collagen, formed and/or secreted by the cells and then tanning (e.g., chemically cross-linking). Tanning may be performed after the scaffold fibers have been at least partially covered in cultured cells and extracellular matrix released by the cultured cells.

In general, because they are intended for use as part of a textile, any of the scaffolding materials described herein may be non-biodegradable, at least over the immediate term (e.g., within 1 year, 2 years, 5 years, 10 years, etc.) of ordinary use.

As will be described in greater detail below, the density of tissue (e.g., cells and extracellular material deposited by the cells, particularly collagen) on the substrate should be greater than a minimum threshold in order for the resulting material (equivalently referred to herein as artificial leather, synthetic leather or cultured leather) that is greater than about 200,000 cells/cm$^2$ of substrate surface area immediately prior to tanning the material using any of the modified tanning (e.g., cross-linking) steps described herein. For example, the density of the cells may be between about 200,000 to about 4,500,000n cells/cm$^2$, or from about 250,000 to about 4,000,000 cells/cm$^2$, or from about 500,000 to about 2,000,000 cells/cm$^2$ of substrate surface area (e.g., between an upper and lower boundary where the lower boundary is 200,000 cells/cm$^2$, 250,000 cell/cm$^2$, 300,000 cells/cm$^2$, 400,000 cells/cm$^2$, 500,000 cell/cm$^2$, etc. of substrate surface area and the upper bound is 1,000,000 cells/cm$^2$, 1,500,000 cells/cm$^2$, 2,000,000 cells/cm$^2$, 3,000,000 cells/cm$^2$, 4,000,000 cells/cm$^2$, 5,000,000 cells/cm$^2$, 6,000,000 cells/cm$^2$, etc., of substrate surface area, where the upper bound is always greater than the lower bound). If the density is too low or too high, the leather will not have the desired quality/tensile strength. Once processed by cross-linking (tanning) and/or lubricating/fatliquoring, the material may comprise a tanned fibrous scaffolds comprising a plurality of fibers, wherein the fibers are surrounded by extracellular matrix cross-linked to the plurality of fibers at a density of greater than a minimum that is, e.g., 0.01 µm or greater (e.g., 0.02 µm or greater, 0.03 µm or greater, 0.04 µm or greater, 0.05 µm or greater, 0.06 µm or greater, 0.07 µm or greater, 0.08 µm or greater, 0.09 µm or greater, 0.1 µm or greater, 0.2 µm or greater, 0.3 µm or greater, 0.4 µm or greater, 0.5 µm or greater, 0.6 µm or greater, 0.7 µm or greater, 0.8 µm or greater, 0.9 µm or greater, 1 µm or greater, 2 µm or greater, 3 µm or greater, 4 µm or greater, 5 µm or greater, 6 µm or greater, 7 µm or greater, 8 µm or greater, 9 µm or greater, 10 µm or greater, etc., including between 0.01 µm and 200 µm, etc.), wherein there is good adhesion between the extracellular matrix and the plurality of fibers so that the tensile strength of the fiber-reinforced biological tissue composite material is greater than about 1.0 MPa. In general, these materials (artificial leathers) may be tanned an may have a water content that is less than 30%, less than about 25%, less than about 20%, less than about 18%, less than about 15%, less than about 12%, less than about 10%, less than about 7%, less than about 5%, etc. Thus, the fiber-reinforced biological tissue composite material may be dehydrated.

Although the amount of water in the initial culture is greater than 95%, this water must be removed to form the composite material (e.g., artificial leather, cultured leather, or synthetic leathers described herein). The tanning (crosslinking) process described herein typically include a dehydration/drying step that removes the majority of the water, so that the final amount of water left in the resulting composite material is between from about 1% to about 10% (e.g., from about 2% to about 8%, or from about 3% to about 7%, etc.) by weight. If the water content is too low, the resulting material (leather) will be brittle. If the water content is too high, the resulting material (leather) may be susceptible to microbial growth. In addition, the resulting material may be further processed to apply a lubricant material (e.g., by the addition and/or impregnation with a hydrophobic material (such as an oils, including sulfonated oils, wax, fat, etc.) such as may occur by a modified fatliquoring process. In any of the methods described herein a finishing step of impregnating the material (including soaking, coating, etc. with or without a pH and/or heating step) may be performed. They hydrophobic material (including one or more of oil, wax, fat, etc.) may be included in the final product in an amount that is between about 0.001% and about 15% (such as equal to or between about 0.1% and about 12%, e.g., having a lower bound of 0.001%, 0.01%, 0.1%, 0.5%, 1%, 2%, 3%, etc. and an upper boundary of 15%, 14%, 13%, 12%, 11%, 10%, 9%, 8%, etc., where the lower boundary is always less than the upper boundary) by weight. For example, any of the materials formed as described herein may include between about 0.1% and about 12% of a hydrophobic material (such as one or more of an oil, fat, wax, etc.).

In general, the scaffolds described herein are fibrous scaffolds formed of any material (including any crosslinkable material) that is conducive for cell growth and collagen tissue formation, but particularly protein materials (e.g., containing amine, carboxylic acid, sulfhydryl and hydroxyl groups), such as silk, in order to promote or stabilize interactions (both covalent and non-covalent) between the scaffold and the collagen tissue. Silk is an example of a fibrous scaffold. Silk is generally formed of a protein fiber that may be composed mainly of fibroin. For example, silk fibers from domesticated silkworms typically have a triangular cross section with rounded corners, 5-10 µm wide. The fibroin-heavy chain is composed mostly of beta-sheets, due to a 59-mer amino acid repeat sequence with some variations. Silkworm fibers are naturally extruded from two silkworm glands as a pair of primary filaments (brin), which are stuck together, with sericin proteins that act like glue, to form a bave. Bave diameters for tussah silk can reach 65 µm. Silk emitted by a silkworm may consist of two main proteins, sericin and fibroin, fibroin being the structural center of the silk, and serecin being the sticky material surrounding it. Fibroin is made up of the amino acids Gly-Ser-Gly-Ala-Gly-Ala and forms beta pleated sheets. Hydrogen bonds form between chains, and side chains form above and below the plane of the hydrogen bond network.

Thus the scaffold may be a protein fiber containing amine and carboxylic acid groups, or a naturally occurring cellulose fibers containing (or modified to contain) amine and carboxylic acid groups. The fibers forming the scaffold may be chemically modified to enhance collagen (released by cultured cells) interactions with the scaffold. For example, the scaffold may be chemically modified to contain groups for crosslinking (covalent or non-covalently) with collagen including amines, carboxylic acids, sulfates, aldehydes, hydrazides, sulfhydryls, epoxides, acrylates, etc. These tissue crosslinking groups may be protected during tissue growth and activated for crosslinking when tissue growth is complete. In particular, the crosslinking referred to herein may be activated during tanning, which may be identical to, or derived from, traditional tanning methods and techniques, including omitting those steps which are made unnecessary by the use of tissue culture as described herein. Further, an additional reinforcement crosslinking step can be used to crosslink chemistries not involved in the traditional tanning process (anything other than amine and carboxylic acid groups). Traditional tanning chemicals can then be used to give the fiber reinforced biological tissue composite a leather-like aesthetic. Scaffolds may also be formed or (and/or may include) carbon fibers, which may also be modified as discussed above.

In general, these tissue crosslinking groups may be pendant to the scaffold with a spacer between 10 daltons and 100 megadaltons. The scaffold may be crosslinked to the tissue through non-covalent interactions including ionic, hydrophobic and van der Waals forces. Alternatively or additionally, the scaffold may be cross-linked to the tissue through covalent bonds. For example, the scaffold may be directly reacted with amine, carboxylic acid and/or hydroxyl groups on the tissue. The scaffold may be reacted with a crosslinker which reacts with amine, carboxylic acid and/or hydroxyl groups on the tissue. The molecular weight of the crosslinker may be between 10 daltons and 100 megadaltons. The tissue referred to herein are the cultured cells and/or the products released by these cultured cells (e.g., extracellular matrix proteins, in particular collagen). Any of the crosslinkers described herein may include a functionality of the crosslinker of between 2 and 2000. In any of the materials formed as described herein a trace amount of the crosslinker used during the formation process may be found in the final material (e.g., less than 0.001%, less than 0.01%, less than 0.1%, etc.); alternatively no trace amount may be found. Thus, the material formed (the artificial leather) may have a residual amount of crosslinker present in the material, such as between 0.0001% and 1% (e.g., less than about 0.1%, less than 0.01%, less than 0.001%, etc., between 0.0001% and 0.01%, etc.).

In general, the scaffold may be composed of fibers. Suitable fibers also include synthetic fibers. Suitable synthetic fibers include, but are not limited to polyester-polyurethane copolymers such as elastane or LYCRA®, polyparaphenylene terephthalamide polymers such as KEVLAR®, nylon polymers such as nylon 6, nylon 6,6 and the like, and polyester polymers such as polyethylene terephthalate. The fibers may be an appropriate size or dimension (e.g., the fibers may have a length of between about 100 nm to 1 m). The fibers may be assembled in a woven or non-woven architecture (or a combination of both). The density of fibers in the scaffold may be between 10 and 10,000 mg/cc. The porosity of the fibrous scaffold may be between 10 and 99%.

Any appropriate cells may be cultured on the fibrous scaffold. The cells may originate from a tissue and/or cell-line. For example, the cells may be of mammalian origin (e.g., bovine, porcine, ovine, etc.). The cells may be of reptile origin (e.g., snake, lizard, etc.). The cells may be of bird origin (e.g., chicken, ostrich, turkey, etc.). The cells may be of fish origin (e.g. shark, etc.). The cells may be of amphibian origin (e.g. frog, salamander, etc.). The cells may be genetically modified (e.g., to increase production of extracellular matrix "ECM", including, e.g., collagen, etc.) or they may be unmodified.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1A the image is shown at a low magnification (scale bar is 1 mm).

FIG. 2A shows the fibrous scaffold and FIG. 2B shows the fibrous scaffold of FIG. 2A following four weeks of fibroblast culture. Cells were seeded onto the silk fiber scaffold shown in FIG. 2A and after four weeks of culture the scaffold fibers are surrounded by tissue (FIG. 2B).

In FIG. 3, a section of scaffold onto which fibroblasts have been cultured (e.g., for four weeks) has been stained with picrosirus red to visualize collagen.

DETAILED DESCRIPTION

Figure 1A:
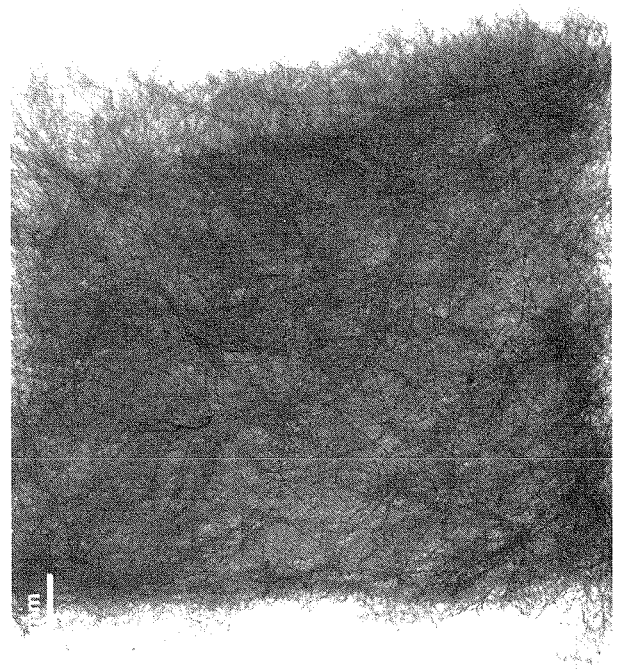
FIG. 1A show a first view of an example of a fibrous scaffold formed of silk fibers that may be used to form the composite manufactured leather described herein.

Described herein are engineered leathers formed using a fibrous scaffold that is tanned (e.g., cross-linked) to the cultured cells and/or any extracellular matrix (ECM) components released by the cultured cells to form. The resulting engineered leather may be referred to as a fiber-reinforced tissue composite and may have superior properties (e.g., durability, strength, etc.) compared to other engineered leathers. Also described are methods of forming these fiber-reinforced tissue composites, including methods of growing/culturing them and methods of tanning them.

In general, the scaffolds described herein are configured to be cross-linked to the released extracellular matrix (e.g., collagen, fibronectin, fibrin, hyaluronic acid, proteoglycans, etc.) from cells cultured on the scaffold. These scaffolds may be formed of a material capable of forming cross-links with ECM and/or the cells during tanning. Further, the structure of the scaffold (e.g., porosity, fiber length, fiber density, etc.) may be chosen to permit cross-linking and/or to encourage growth of the cells and release of extracellular matrix. The scaffold is tanned with and to the ECM to form the final product, the fiber-reinforced tissue composite. Thus, the scaffold forms an integral part of the final product, and its dimensions, including the thickness, may help determine the final thickness of the resulting leather.

One particular example of a fibrous scaffold that may be used as described herein is silk. Silk (e.g., organic and/or synthetic silk) may be formed (e.g., spun) to a predetermine fiber thickness and used in a woven and/or non-woven sheet forming the scaffold onto which ECM-releasing cells may be cultured. Such cells may be, e.g., dermal fibroblasts, smooth muscle cells, etc.

In general, the scaffold is formed of a material (such as silk) that is conducive to cell attachment and tissue growth. In addition the scaffold material can contain surface chemistries that adhere the scaffold fiber to the tissue for effective stress transfer in the final material. Interactions between the scaffold fibers and the tissue can be non-covalent, including electrostatic, hydrophobic, dipole-dipole, induced dipole or van der Walls interactions. These interactions can be tuned through scaffold fiber surface chemistry. In addition, covalent interactions or crosslinks can be introduced to form a chemical bond between scaffold fiber and tissue.

The fibrous scaffold may provide a great deal of surface area onto which cells may be cultured. For example, the scaffold may be formed of relatively dispersed fibers forming a dispersed fibrous scaffold. A fibrous scaffold may have a lot of surface area to allow cell growth and to allow for a strong fiber-tissue matrix interface (which may also enhance overall strength of the resulting composite). In some variations, the length of the fibers forming the scaffold is between 100 nm and 100 μm. In some variations, the length of the fibers is between 100 nm and up to 1 mm, 10 mm, 100 mm or 1 m. The density of the fibrous material in the scaffold may be between 10 and 100 mg/cc. In some variations the density of the fibrous material is between 10 and 10,000 mg/cc. The porosity of the fibrous scaffold (including of the woven/non-woven fibers) may be between 10 and 99%.

In general, it may be advantageous to provide a high porosity. This may permit a lot of cell infiltration and tissue growth, including within the thickness of the scaffold. The scaffold may be any appropriate thickness (e.g., between 10 μm and 5 mm, e.g., between 100 μm and 1 mm, between 100 μm and 500 μm, between 50 μm and 300 μm, etc., or between any lower value of 10 μm, 30 μm, 50 μm, 75 um, 100 um, 200 um, 300 μm, etc. and an upper value of 50 μm, 100 μm, 150 μm, 200 μm, 300 μm, 400 μm, 500 μm, 600 μM, 700 μm, 800 μm, 900 μm, 1 mm, 2 mm, 3 mm, 4 mm, 5 mm, etc.). The porosity may be determined as the space (e.g., average diameter) between fibers.

In operation, the method of forming the fiber-reinforced tissue composites described herein may include culturing cells on the fibrous scaffold until a desired amount of ECM (e.g., collagen) has been formed on and/or over the fibrous scaffold. Optionally, the fibrous scaffold may be formed and/or prepared to receive the cells to be cultured thereon. For example, the scaffold may be treated to expose reactive groups or cell-attachment sites. In some variations the fibrous scaffold may be applied in a cell reactor for seeding and growth of the cells on the scaffold. As an example, cells, which may be, for example, a mammalian cell line having known ECM releasing properties, be seeded onto the prepared fibrous scaffold and allowed to grow, divide and set down ECM. Cells may be cultured in typical culture conditions for an appropriate length of time (e.g., 2-90 days). Additional cells may be added during this period. Thereafter, the resulting material, comprised of the fibrous scaffold with released ECM and cells, may be referred to as an intermediate (untanned) tissue construct, which may be further processed. This intermediate (untanned) tissue construct may be decellularized (e.g., by treatment with alcohols or other agents) or not. The intermediate (untanned) tissue construct may then be processed by tanning, which may include traditional tanning chemistries as well as crosslinking reactions to reinforce the scaffold to the tissue.

Provided below is an example of various reinforcement and tanning methods that may be used and/or modified. The fibrous scaffold and the cultured ECM grown on the scaffold are tanned (and adhered) together by this process, and the resulting fiber-reinforced tissue composites may be used as an engineered leather material.

A reinforcement step may be included to crosslink the deposited ECM to the fibrous scaffold encased in ECM, followed by a tanning procedure to produce the look and feel of traditional leather. While traditional tanning chemistries may effectively crosslink ECM to scaffold if the scaffold has proper functionality (such as surface amine and carboxylic acid groups), other scaffold surface chemistries and cross linkers may be incorporated to strengthen the ECM-scaffold interface. These include epoxide, acrylate, aldehyde, sulfhydryl, diazirines, aryl-azides, etc., as well as protected chemistries that may be activated following tissue growth to reduce cytotoxicity of the scaffold surface. The scaffold may be modified with reactive chemistries prior to cell seeding that are pendant from spacer molecules of size between 0 Da and 100 MDa. The scaffold surface chemistry may be reacted directly to the ECM or through cross linkers with functionality between 1 and 2000 and with size between 1 Da and 100 MDa. Further, crosslinking molecules may be polymerized within the scaffold-ECM construct with a size between 1 Da and 100 MDa. Polymerization of these cross linkers may be initiated following tissue growth with triggers such as light exposure, temperature change, addition of chemical initiators, etc.

In general, any appropriate tanning methods may be used, including method derived from traditional tanning, which may result in leather having the look and feel of traditional tanned hides. For example, following culturing of cells on the scaffolds as described above (e.g., in a sterile environment), the intermediate (untanned) tissue construct consisting of cells and ECM grown on the planar (e.g., relatively thin, but long and wide sheet of) fibrous scaffold may be washed (e.g., to remove culture medium), and tanned. Traditional steps such as liming (e.g., treatment with a basic compound such as milk of lime and/or the addition of "sharpening agents" including disulfide reducing agents such as sodium sulfide, cyanides, amines, etc.) may be included. Such steps may be modified, however, as the intermediate construct does not include hair, nail and other keratinous matter typically found in native skins. Such steps may be maintained or modified to remove some ECM materials and/or to swell and split fibers in the intermediate construct or otherwise prepare collagen in the construct for tanning.

The methods may include or avoid (as unnecessary) the use of unhairing agents such as sodium sulfide, sodium hydroxide, sodium hydrosulfite, calcium hydrosulfide, dimethyl amine, and sodium sulfhydrate.

A step that removes cellular material while preserving the ECM may also be included. Decellularization methods used in tissue engineering may be used for this purpose including the use of surfactants, enzymes, ultrasonic energy, freeze thaw cycles, etc.

A deliming step may also be included. For example, the pH of the collagen may be brought down to a lower level so that enzymes may act on it. Depending on the end use of the leather, the intermediate construct may be treated with enzymes to soften them, a process called bating. If bating is used, once completed, the intermediate tissue construct may be treated first with salt and then with sulfuric acid, if a mineral tanning is to be done, which may bring down the pH of collagen to a very low level so as to facilitate the penetration of mineral tanning agent into the substance. This process is known as pickling. The salt (e.g., sodium chloride) may penetrate faster than the acid and limit the ill effect of sudden drop of pH. If vegetal tanning is used, the tanning agent may be tannin. The tannins are a class of polyphenol astringent chemicals that occur naturally in the bark and leaves of many plants. Tannins bind to the collagen proteins and may hide and coat them, causing them to become less water-soluble and more resistant to bacterial attack. The process may also cause the material to become more flexible. Traditionally, primary barks, processed in bark mills and used in modern times, are chestnut, oak, redoul, tanoak, hemlock, quebracho, mangrove, wattle, and myrobalans. Traditionally, hides are stretched on frames and immersed for several weeks in vats of increasing concentrations of tannin. The intermediate tissue constructs described herein may provide easier, more direct access to the tannins and may therefore require less processing time in general.

In chrome tanning, prior to the introduction of the basic chromium species, several steps may be used to prepare the material, as mentioned above, including the introduction of alkali agents such as sodium hydroxide, restoring neutral pH, bating (softening with enzymes), and pickling (lowering pH of the material being processed, e.g., with salt and sulfuric acid).

In traditional tanning, the pH is very acidic when the chromium is introduced, to ensure that the chromium complexes are small enough to fit in between the fibers and residues of the collagen. Once the desired level of penetration of chrome into the substance is achieved, the pH of the material is raised again to facilitate the process. This step is known as basification. Chrome tanning is typically faster than vegetable tanning.

Chromium(III) sulfate ($[Cr(H_2O)_6]_2(SO_4)_3$) has long been regarded as the most efficient and effective tanning agent. Chromium(III) compounds of the sort used in tanning are significantly less toxic than hexavalent chromium. Chromium(III) sulfate dissolves to give the hexaaquachromium(III) cation, $[Cr(H_2O)_6]^{3+}$, which at higher pH undergoes processes called olation to give polychromium(III) compounds that are active in tanning, being the cross-linking of the collagen subunits. The chemistry of $[Cr(H_2O)_6]^{3+}$ is complex due to the presence of a variety of ligands. Some ligands include the sulfate anion, the collagen's carboxyl groups, amine groups from the side chains of the amino acids, and masking agents. Masking agents are carboxylic acids, such as acetic acid, used to suppress formation of polychromium(III) chains. Masking agents allow the tanner to further increase the pH to increase collagen's reactivity without inhibiting the penetration of the chromium(III) complexes.

As mentioned above, collagen is characterized by a high content of glycine, proline, and hydroxyproline, usually in the repeat -gly-pro-hypro-gly-. These residues give rise to collagen's helical structure. Collagen's high content of hydroxyproline allows for significant cross-linking by hydrogen bonding within the helical structure. Ionized carboxyl groups (RCO2-) are formed by hydrolysis of the collagen by the action of hydroxide. This conversion occurs during the liming process, before introduction of the tanning agent (chromium salts). The ionized carboxyl groups coordinate as ligands to the chromium(III) centers of the oxohydroxide clusters.

Tanning increases the spacing between protein chains in collagen from 10 to 17 Å. The difference is consistent with cross-linking by polychromium species, of the sort arising from olation and oxolation.

Subsequent to application of the chromium agent, the bath may be treated with sodium bicarbonate to increase the pH to 4.0-4.3. This increase induces cross-linking between the chromium and the collagen. The pH increase may normally be accompanied by a gradual temperature increase up to 40° C. Chromium-tanned leather can contain between 4 and 5% of chromium. This efficiency is characterized by its increased hydrothermal stability of the leather, and its resistance to shrinkage in heated water.

Other forms of tanning may be used, including ones based on alum, zirconium, titanium, iron salts, or a combination thereof. Tawing may be used on the intermediate tissue constructs described herein. Tawing is a method that uses alum and aluminum salts, generally in conjunction with other products such as egg yolk, flour, and other salts. The material becomes tawed by soaking in a warm potash alum and salts solution (or equivalent), between 20 and 30° C. The process may increase the resulting leather's pliability, stretchability, softness, and quality. Adding egg yolk and flour (or equivalents) to the standard soaking solution may further enhance its fine handling characteristics. Then, the intermediate tissue construct is dried and allowed to stabilize.

Depending on the finish desired, the material may be waxed, rolled, lubricated, oiled (e.g., injected with oil), and/or dyed. Suedes, nubucks, etc. may be formed, e.g., by inducing surface finishes. The material may be additionally finished by retawing. Retawing agents and/or dyes may be applied to the material to enhance the physical strength and properties desired depending on the end product. A final stage, finishing, may be used to apply finishing material to the surface or finish the surface.

Once cells on the fibrous scaffold have been grown to the proper density so that the resulting material (once tanned) to have the desired strength (e.g., greater than about 200,000 cells/cm$^2$ of substrate surface area) and the 'wet' material has been formed, it may be tanned, as described above, using any of the tanning (or modified tanning procedures mentioned. In addition, the material is typically treated by one or more other post-culturing processes (which may be performed with the tanning steps mentioned above, or after the tanning steps).

For example, fatliquoring may include the addition of natural or synthetic lubricants to the fibers prior to forming them into a textile, which not only allow the fibers of the material to dry without interfacial adhesion (sticking) but may also provide hydrophobicity, and other properties, to the material. The methods described herein may provide advantages over regular fatliquoring, in that the material, which may have a predictable and highly regular structure/fiber density, may be definitively treated with a set amount of lubricant (hydrophobic material, e.g., oil, wax, fat, etc.) to ensure uniform and/or regular penetration, which is not guaranteed with natural leather due to the variability in internal fiber structure. These methods may also allow for alternate lubricants to be used that could not be normally considered due to issues with dispersion size, i.e., in natural leather for deep fiber penetration the emulsion size may be critical in order to be small enough to penetrate fully within the fiber matrix, but this may be alleviated by treating fibers individually as described herein. Further these methods may also provide improved tensile and tearing strength characteristics due to highly efficient fatliquoring. Finally the methods described herein may provide nearly complete (e.g., 100%) efficiency in exhaustion of the reagent, including the lubricant; in addition, the lubricant may be virtually immediately reacted with the material, as opposed to having to penetrate and then fix the lubricant as required by in natural leather. This results in an extremely energy efficient and material efficient process, using less chemicals, lower temperatures (as 'cold' fatliquoring may be employed or alternatively hot/warming of the material may be performed) and reduced water usage which consequently will reduce effluent requirements. In some variations, the percentage of fatliquoring (e.g., the percentage of oil lubricant by weight) may be less than 12% (e.g., between 0.1-15%, between 0.5-10%, etc. by weight of the material). In addition, one or more lubricants may be incorporated into the material itself during the formation process, including prior to tanning. In some variations the fatliquoring may be performed immediately after tanning the material. Examples of fatliquoring agents may include: oils (e.g., sulfonated oils, mineral oil, etc.), fats (animal fats, vegetable fats, e.g., glycerides, etc.), synthetic lubricants, polysiloxanes, lubricating acrylic polymers, dry lubricants, etc. The fibers and/or a textile made from the fibers described herein may be made water resistant (e.g., "waterproofing") by the addition of an agent such as a hydrophobic agent, which can include, but are not limited to, hydrophobic lubricants (e.g. a modified polysiloxane such as Densodrin CD from BASF), fluorocarbons, hydrophobic acrylic polymers, chromium stearates, etc. The ability to make each fiber water resistant may also increase the consistency and varying levels of water resistance may be achievable in a controlled manner.

Interestingly, in some variations, the materials described herein may be used to form a cultured leather without fatliquoring as a separate, post-culturing step. For example the fibrous tissue scaffold material may include a material that provides sufficient moisture retention and/or hydrophobicity to avoid the necessity for additional fatliquoring. For example, the fibers forming the scaffolding material may be hydrophobic. Mildly hydrophobic tissue scaffolds may include polymers (e.g., aliphatic polyesters, etc.).

Retanning is performed with traditional leather materials to modify the qualities of the leather, including increasing/decreasing the concentration of the tanning agent, and/or modify the properties of the resulting fibers and/or textiles which may in term enhance further processing of the material, including dying. In any of the methods described herein retanning may be performed with the same or a different tanning agent. Retanning may be performed on the material.

Retanning may be combined with any of the other steps described herein, including fatliquoring and/or dyeing. In addition, the order of these steps may be performed in any appropriate sequence (e.g., retanning then fatliquoring, etc.).

Dyeing adds color to the fibers and/or the resulting textile. Any appropriate dye may be used, particularly dyes that are appropriate for leather (e.g., collagen materials although other dyes specifically designed for textiles are may be used including those that have compatible reactivity, e.g. reactive dyes. As mentioned, in some variations a dye or dyes may be included in the culturing solution prior to tanning or immediately after tanning. Dyes may include acid dyes (e.g., pre-metallized acid dyes), basic dyes, direct dyes, reactive dyes and sulfur dyes. A mordant dye (e.g., including a mordant to help with binding of the dye to the material) may also be used.

Other chemical treatments may also be added such as: flame retardants, abrasion resistance treatments, thermosregulating technologies, moisture management technologies, performance particulates, etc.

EXAMPLES

FIGS. 1-6 illustrate example of fiber-reinforced tissue composites and methods of forming them as described above.

Figure 1B:
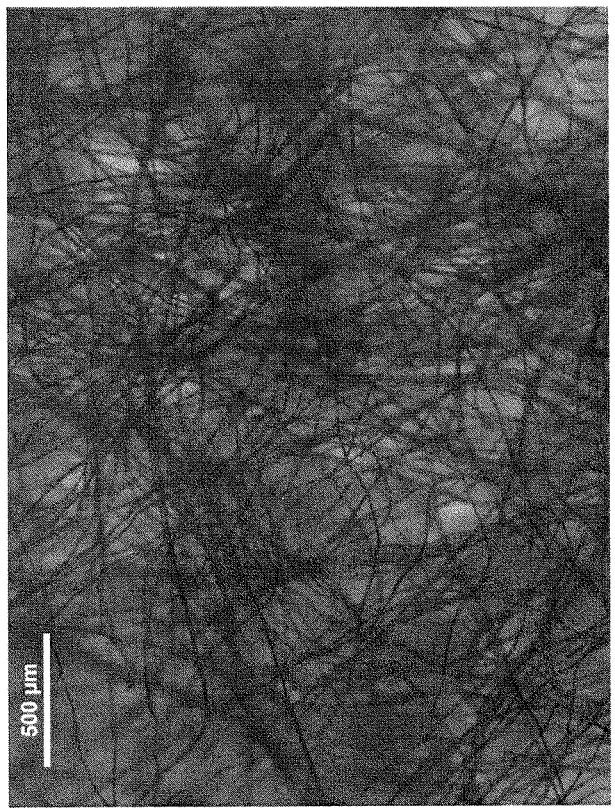
FIG. 1B shows the fibrous scaffold of FIG. 1A at higher magnification (scale bar is 0.5 mm).

For example, FIGS. 1A and 1B show an example of a fibrous tissue scaffold that may be used. In this example, the scaffold is formed of silk fibers. The scaffold has a thickness of about 0.5 mm, and fiber diameters of about 15-20 microns (e.g., on average/mean). In this example, the overall material density is approximately 80 mg/cc, which corresponds to a porosity of about 95%. The orientation of fibers may affect overall materials properties, and the assembly process may be varied to produce a variety of non-woven, woven and knit architectures. In addition, the length of the fibers may affect overall material properties, and the fiber length, diameter and/or porosity may be varied. For example, microfibers may be used having a diameter from about 10 µm (microns) to 20 µm or more. FIG. 1B shows an enlarged view of a region of the scaffold shown in FIG. 1A.

Figure 2A:
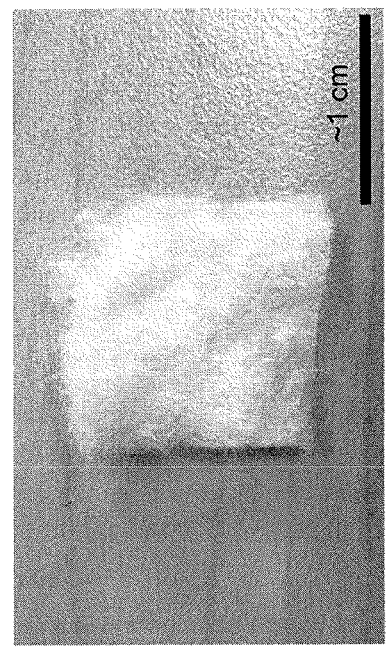
FIGS. 2A and 2B illustrate tissue growth on a fibrous scaffold such as the silk scaffold shown in FIGS. 1A-1B.
Figure 2B:
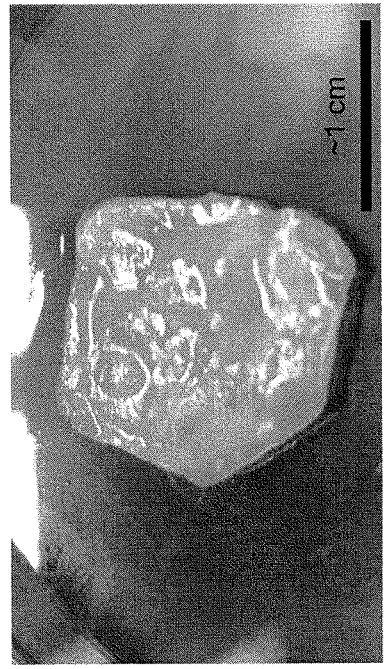

FIG. 2A shows an example of a "dry" fibrous (silk) scaffold prior to seeding with cells. In FIG. 2B, the scaffold shown in FIG. 2A has been seeded with cells (in this example, bovine dermal fibroblasts) at density of $8.5 \times 10^6$ cells/ml. The volume of the seeded cells was 100 µL/cm$^2$ of scaffold (similar to that shown in FIG. 1A-1B). In this example, cells are seeded on top of the scaffold and have been seen to settle (e.g., via gravity) onto the porous scaffold. Thereafter, the scaffold can be turned, flipped, rotated, etc., which may help distribute the cells and/or culture medium throughout the substrate. In practice it may be beneficial to have a fibrous substrate that is initially greater than 50% porous. As mentioned above, in some variations, the scaffold may be modified to enhance cell attachment.

In the example, shown in FIG. 2B, the cells may be cultured for approximately 4 weeks, with regular change in media (e.g., every few days); standard tissue culture techniques may be adapted for use with the scaffold; for example, growth factors may be used, or agents to enhance the release and/or type of ECM deposited. In addition, dynamic culture environments such as perfusion or mechanical loading may be used to enhance ECM deposition. In FIG. 2A-2B, the scaffold has a thickness of about 0.5 mm. Thicker scaffolding may also be used (e.g., up 5 cm).

After four weeks of culture the scaffold fibers are surrounded by tissue (including collagen).

Figure 3:
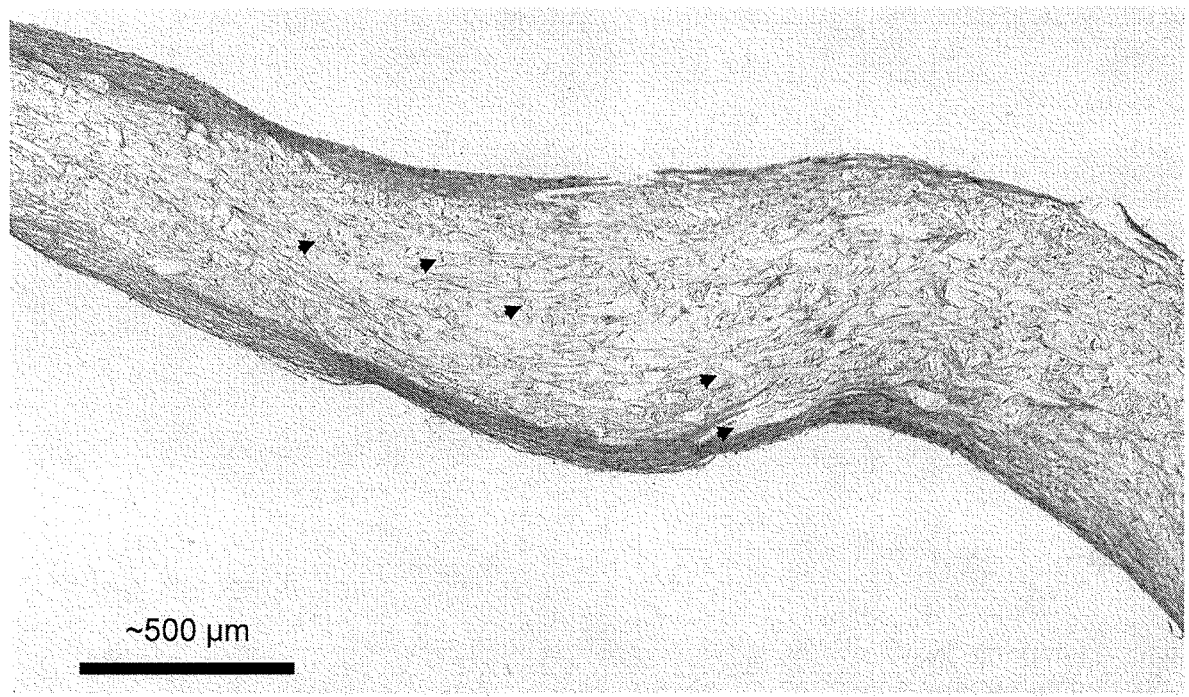
FIG. 3 shows an example of a silk scaffold onto which fibroblasts have been cultured, prior to tanning.

FIG. 3 shows a section taken from the exemplary intermediate (untanned) tissue construct shown in FIG. 2B in cross-section through the tissue. In this example the stain shows (red in original color version) collagen; scaffold fibers are indicated (in section) by the arrowheads. The sample is shown having a dense network of collagen extending around and through (e.g., within the porous fibrous scaffold). This sample was fixed for histology. A scanning electron microscopic image of an intermediate (untanned) tissue construct similar to that shown in FIG. 2B is provided in FIG. 4.

Figure 4:
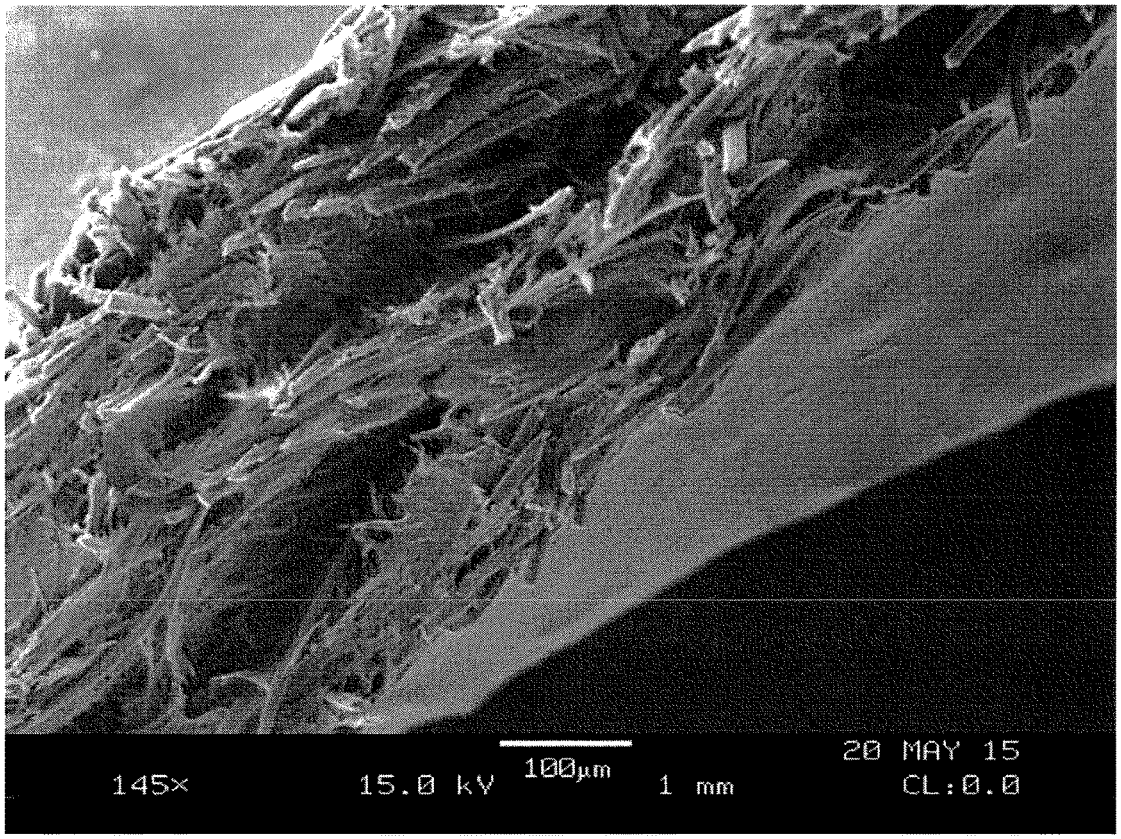
FIG. 4 is a scanning electron micrograph showing a portion of a fibrous silk scaffold onto which fibroblasts have been grown and allowed (and in some variations stimulated) to secrete collagen. Collagen rich tissue has grown throughout the silk fiber scaffold.

In FIG. 4, a section through a fibrous scaffold onto which cells releasing collagen have been cultured is shown. The fibrous scaffold in this example is silk, and the SEM shows collagen-rich tissue grown throughout the silk fiber scaffold.

Figure 5:
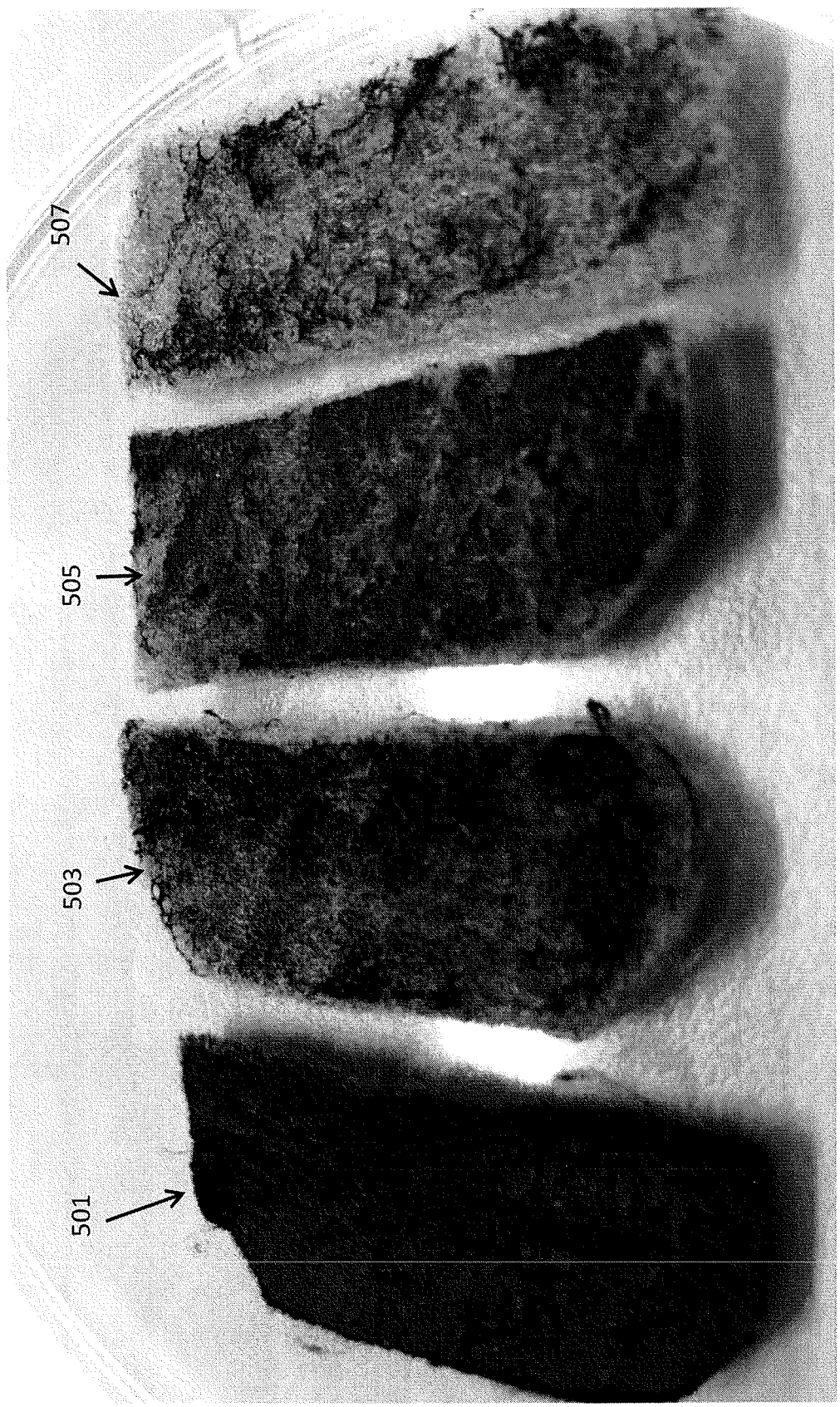
FIG. 5 shows examples of four different composites of fibrous scaffolds (silk, high density PLLA, polyester, low density PLLA) and fibroblasts after eight weeks of culture, followed by tanning. Only the fibrous silk scaffold composite was successfully tanned into a leather like material. This could be due to the presence of amine, carboxylic acid and hydroxyl groups on the silk protein, although differences in the amount and type of tissue formed on the different scaffolds cannot be ruled out.

FIG. 5 shows a comparison between different fibrous scaffolds for tissue culture and subsequent tanning into a leather-like material. In FIG. 5 the silk scaffold was much more successful than the polylactic acid, PLLA, scaffold; the silk scaffold allowed reinforcement crosslinking during a tanning process as described herein. In FIG. 5, cells have been cultured equivalently on four different fibrous scaffolds and tanned: silk 501, high density PLLA 503, polyester 505, and low density PLLA 507. Only the silk scaffold included amine and carboxylic acid groups which may crosslink with the tissue/ECM during the tanning process (chromium salt tanning). There are also differences in the fiber density and ability of these materials to promote tissue growth. These scaffolds were each about 4 cm long and about 1.5 cm wide; the silk 501 and low density PLLA 507 are each 0.5 mm thick and the high density PLLA and polyester are each about 1 mm thick. Following tanning, only samples in which the scaffold was cross-linkable when tanning (e.g., silk 501) resulted in materials having a texture and look similar to native leather. Tanned silk without cells cultured on it does not look similar to native leather; the resulting material (silk alone) pulls apart.

Figure 6:
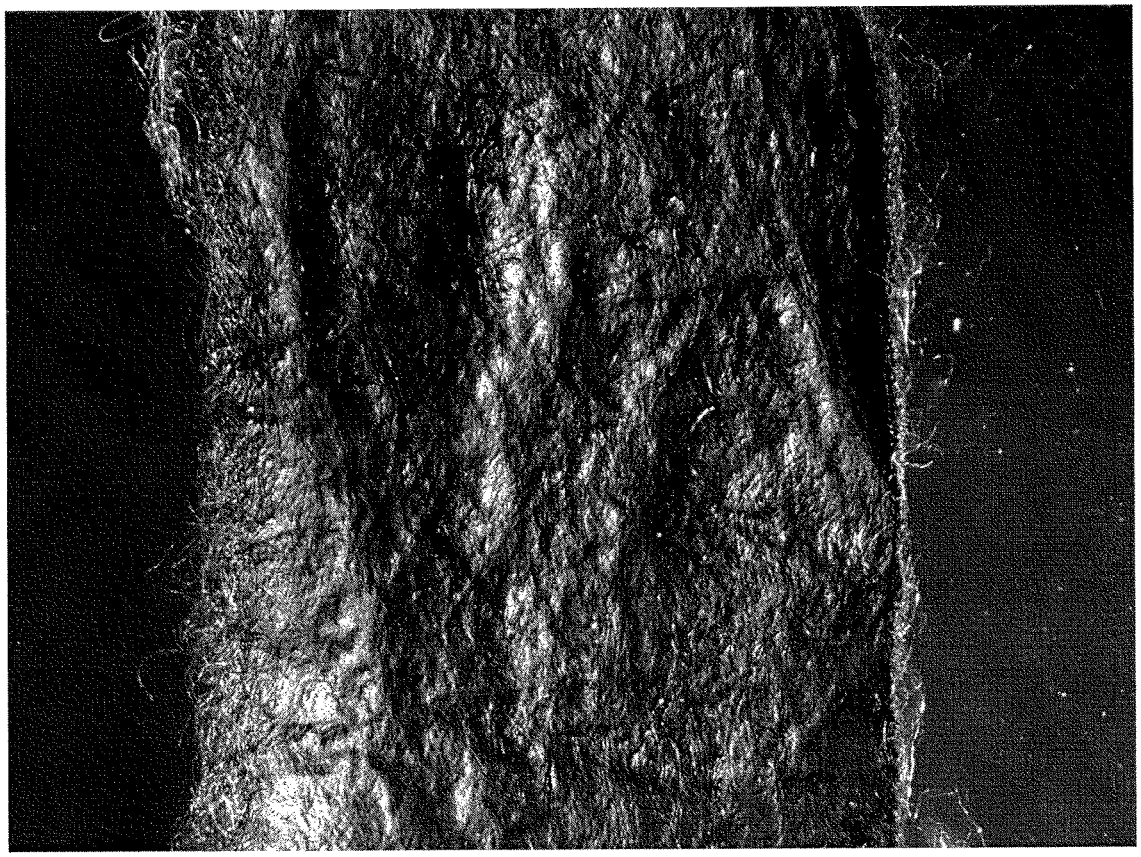
FIG. 6 shows an example of the leather-like surface of a fibrous silk scaffold composite after tanning.
Figure 7:
FIG. 7 is an example of the edge of a fibrous silk scaffold composite after tanning, in which a gradient of tissue was produced towards the edge of the silk scaffold, revealing the silk fibers dispersed throughout the tissue matrix.

FIGS. 6 and 7 illustrate example of fiber-reinforced tissue composites formed as described herein after tanning. FIG. 6 shows an outer surface of a tanned material that has been formed and processed as described above. In this example, the leather-like outer surface feels similar to native leather. The material is formed of a silk fibrous scaffold onto which cells (dermal fibroblasts) have been cultured, and the resulting intermediate tissue construct has been tanned. FIG. 7 shows an enlarged view of an edge region of a tanned (silk) fiber-reinforced tissue construct. After tanning, a gradient of tissue was produced toward the edge of the silk scaffold, revealing the silk fibers dispersed through the tissue matrix (on the right in the figure).

In general, the resulting product will have a look and feel similar to native leather, but is detectably (e.g., under examination of the ultrastructure) different. For example, the resulting material will have the fibrous scaffold material dispersed throughout, and typically surrounded by ECM (e.g., collagen); the collagen and the scaffold are both tanned and adhered together. There will typically be an outer layer of tissue on the scaffold. The sample may be tested for tensile strength using and Instron machine. Clamps are attached to the ends of the sample and the sample is pulled in opposite directions until failure. Good adhesion is demonstrated when the sample has a tensile strength of at least 1 MPa. In any of the variations described herein, the final material (leather) produced as described herein may have a desirable range of properties due to the unique method of processing/manufacture described herein. For example, in any of the materials described herein the material may have a tensile strength (estimated as described above) of greater than about 0.5 MPa, greater than about 0.6 MPa, greater than about 0.7 MPa, greater than about 0.8 MPa, greater than about 0.9 MPa, greater than about 0.95 MPa, greater than about 1.0 MPa, greater than about 1.1 MPa, greater than about 1.2 MPa, greater than about 1.3 MPa, greater than about 0.4 MPa, greater than about 1.5 MPa, etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprise" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of forming a fiber-reinforced composite material, the method comprising:
   culturing cells selected from the group consisting of mammalian cells, reptile cells, fish cells, bird cells, and amphibian cells, on a fibrous scaffold until a plurality of fibers of the fibrous scaffold are surrounded by tissue comprising collagen at a density of greater than about 200,000 cells/cm' of scaffold surface area; and
   tanning the cultured scaffold to form a fiber-reinforced composite material,
   wherein the fibers of the fibrous scaffold have a surface functional group,
   wherein the collagen is cross-linked to the surface functional group on the plurality of fibers,
   wherein the cross-linking between the functional group of the plurality of fibers and the collagen is sufficient to create the fiber-reinforced composite material comprising a tensile strength that is greater than about 1.0 MPa, and
   wherein the scaffold comprises a naturally occurring cellulosic fiber containing the surface functional group, further wherein the surface functional group is selected from the group consisting of: an amine, a hydroxyl group, a carboxylic acid group, and combinations thereof.

2. The method of claim 1, wherein the scaffold comprises a synthetic fiber.

3. The method of claim 1, wherein the tanning comprises crosslinking the collagen to the scaffold.

4. A fiber-reinforced composite material, the material comprising:
   a tanned fibrous scaffold comprising a plurality of fibers having a surface functional group,
   wherein the plurality of fibers are surrounded by collagen cross-linked to the surface functional group on the plurality of fibers,
   wherein the cross-linking between the surface functional group of the plurality of fibers and the collagen is sufficient to create a fiber-reinforced composite material having a tensile strength that is greater than about 1.0 MPa, and
   wherein the scaffold comprises a naturally occurring cellulosic fiber containing the surface functional group, further wherein the surface functional group is selected from the group consisting of: an amine, a hydroxyl group, a carboxylic acid group, and combinations thereof.

5. The material of claim 4, wherein the scaffold comprises a naturally occurring protein fiber containing the surface functional group.

6. The material of claim 4, wherein the scaffold comprises a synthetic fiber.

7. The material of claim 4, wherein the plurality of fibers are chemically modified to enhance adhesion of the collagen to the scaffold.

8. The material of claim 4, wherein the surface functional group is protected during tissue growth and activated for crosslinking when tissue growth is complete.

9. The material of claim 4, wherein the surface functional group is a crosslinker, and
   wherein the material comprises between 0.0001% and 0.1% of the crosslinker.

10. The material of claim 4, further comprising a leather dye.

11. The material of claim 10, wherein the leather dye is selected from the group consisting of: an acid dye, a basic dye, a direct dye, a reactive dye, a sulfur dye, a mordant dye, and combinations thereof.

12. The material of claim 4, further comprising a fatliquoring agent.

* * * * *